United States Patent
Komann et al.

(10) Patent No.: US 12,383,667 B2
(45) Date of Patent: *Aug. 12, 2025

(54) HOLDING DEVICE HAVING A TOTAL HEIGHT $R_t$ OF A ROUGHNESS PROFILE

(71) Applicant: SCHOTT Pharma Schweiz AG, St. Gallen (CH)

(72) Inventors: Christian Komann, Speicher (CH); Ulrich Walcher, St. Gallen (CH)

(73) Assignee: SCHOTT Pharma Schweiz AG, St. Gallen (CH)

( * ) Notice: Subject to any disclaimer, the term of this patent is extended or adjusted under 35 U.S.C. 154(b) by 287 days.

This patent is subject to a terminal disclaimer.

(21) Appl. No.: 18/098,855

(22) Filed: Jan. 19, 2023

(65) Prior Publication Data

US 2023/0302217 A1    Sep. 28, 2023

(30) Foreign Application Priority Data

Jan. 28, 2022 (EP) .................................... 22154057

(51) Int. Cl.
| | | |
|---|---|---|
| *A61M 5/00* | (2006.01) | |
| *A61J 1/16* | (2023.01) | |
| *B65D 25/10* | (2006.01) | |

(52) U.S. Cl.
CPC ............... *A61M 5/008* (2013.01); *A61J 1/16* (2013.01); *B65D 25/108* (2013.01)

(58) Field of Classification Search
CPC ...... A61M 5/008; A61M 5/002; A61M 5/001; A61M 2205/0222; A61M 2207/00;
(Continued)

(56) References Cited

U.S. PATENT DOCUMENTS

| | | | |
|---|---|---|---|
| 8,800,800 B2 * | 8/2014 | Gerner ................. | B65D 25/108 211/71.01 |
| 2014/0014654 A1 | 1/2014 | Gerner et al. | |

(Continued)

FOREIGN PATENT DOCUMENTS

| | | |
|---|---|---|
| WO | 2014/049712 A1 | 4/2014 |
| WO | 2014/112113 A1 | 7/2014 |

OTHER PUBLICATIONS

"3.2.1 Glass Containers for Pharmaceutical Use", European Pharmacopoeia 9.6, Jan. 2019 (7 pages).
(Continued)

*Primary Examiner* — King M Chu
(74) *Attorney, Agent, or Firm* — TAYLOR & EDELSTEIN, PC

(57) ABSTRACT

A holding device, for holding a plurality of primary packaging containers for pharmaceutical, medical, or cosmetic compositions, includes: a plate-shaped carrier element which includes a plurality of through-holes; a plurality of receptacles, each being configured for accommodating a respective one of the plurality of primary packaging containers, each of the plurality of receptacles including a longitudinal direction and a receptacle wall which partially encloses a receptacle interior and forms a wall body, the wall body extending in the longitudinal direction through a respective one of the plurality of through-holes and, for each of the plurality of receptacles, having an interior surface which faces the receptacle interior and an exterior surface which faces opposite to the interior surface, at least 50% of respective ones of the plurality of receptacles having a maximum total height $R_t$ of a roughness profile of the interior surface which is not more than 0.50 mm.

19 Claims, 17 Drawing Sheets

(58) Field of Classification Search
CPC .... A61J 1/16; B65D 25/108; B32B 2307/538; B32B 27/08; B32B 2307/732; A61L 27/06; A61L 2/00
USPC .............. 206/446, 443; 428/141; 211/74; 220/507
See application file for complete search history.

(56) References Cited

U.S. PATENT DOCUMENTS

| | | | |
|---|---|---|---|
| 2015/0182686 A1 | 7/2015 | Okihara | |
| 2018/0126066 A1 | 5/2018 | Narvekar et al. | |
| 2018/0328492 A1* | 11/2018 | Kustermans | F16J 15/3232 |

OTHER PUBLICATIONS

"Part 1: Injection vials made of a glass tubing", DIN EN ISO 8362-1:2009 + A1:2015, Jun. 2016 (15 pages).
"Injection equipment for medical use—Part 1: Ampoules for injectables", DIN ISO 9187-1:2010(E), Fourth edition Oct. 15, 2010 (16 pages).
"Part 4: Glass barrels for injectables", DIN ISO 11040-4:2007-10, Oct. 2007 (14 pages).
"Part 1: Glass cylinders for pen-injectors for medical use", DIN ISO 13926-1:2004, Oct. 2005 (7 pages).
"Prefilled Syringes—Part 1: Glass cylinders for dental local anaesthetic cartridges", DIN ISO 11040-1, Dec. 1, 2015 (12 pages).
"Standard Practice for Performance Testing of Shipping Containers and Systems", ASTM Designation: D4169-16 (17 pages).
"Standard Test Methods for Rough Handling of Unitized Loads and Large Shipping Cases and Crates", ASTM Designation: D6179-07, Reapproved 2014 (6 pages).
"Standard Test Method for Random Vibration Testing of Shipping Containers", ASTM Designation: D4728-17 (6 pages).
"Improvement of adhesion properties of polypropylene substrates by methyl methacrylate UV photografting surface treatment", J. Balart et al., Materials and Design, vol. 33, London GB, Jun. 30, 2011, pp. 1-10 (10 pages).
"Scratch tests on micro-structured polymer surfaces produced by injection molding and reaction processes", Sandra Kuhn et al., Journal of Micromechanics and Microengineering, Institute of Physics Publishing, vol. 21, No. 6, Bristol GB, May 18, 2011 (12 pages).
"Durabilty of Polymer Gear-Paired with Steel Gear Manufactured by Wire Cut Electrical Discharge Machining and Hobbing", Alexis Johnney Mertens et al., International Journal of Precision Engineering and Manufacturing, Korean Society for Precision Engineering, vol. 17, No. 2, pp. 181-188, Feb. 2016 (8 pages).
"Injection Molding Handbook", Dominick V. Rosato, P.E. et al., Kluwer Academic Publishers, Boston, Jan. 1, 2000, pp. 1-1457 (1481 pages).
Translation of WO 2014/049712 A1 issued Apr. 3, 2014 (17 pages).
Translation of WO 2014/112113 A1 issued Jul. 24, 2014 (8 pages).
European Communication pursuant to Article 94(3) EPC dated Aug. 5, 2022 for European Patent Application No. 22 154 057.8 (10 pages).

* cited by examiner

100

300

304

700

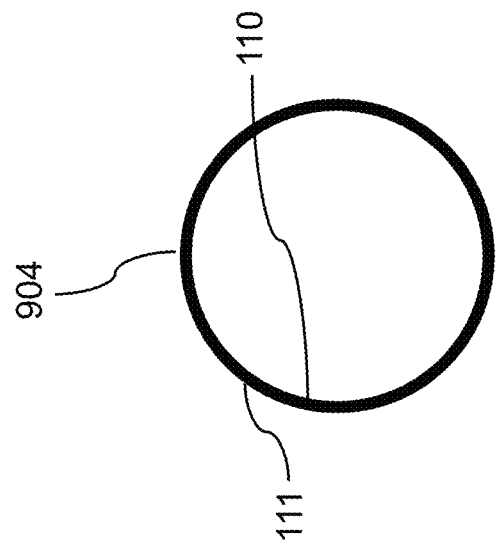
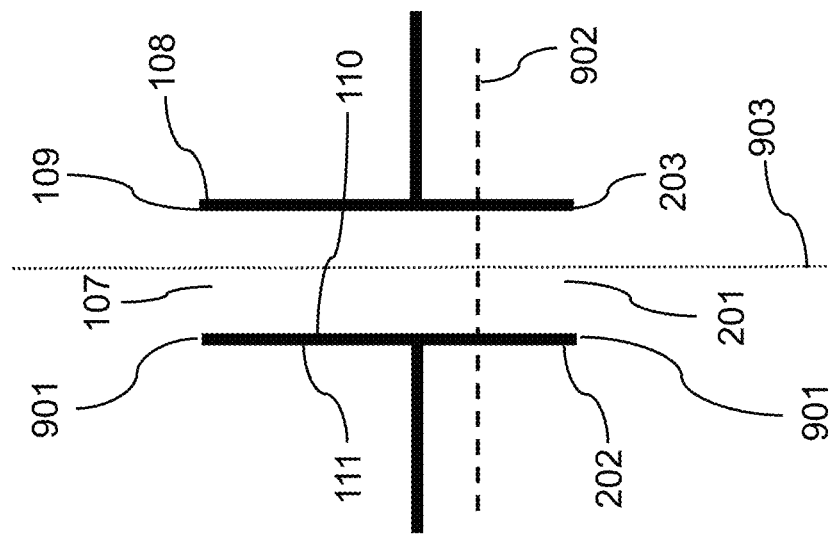

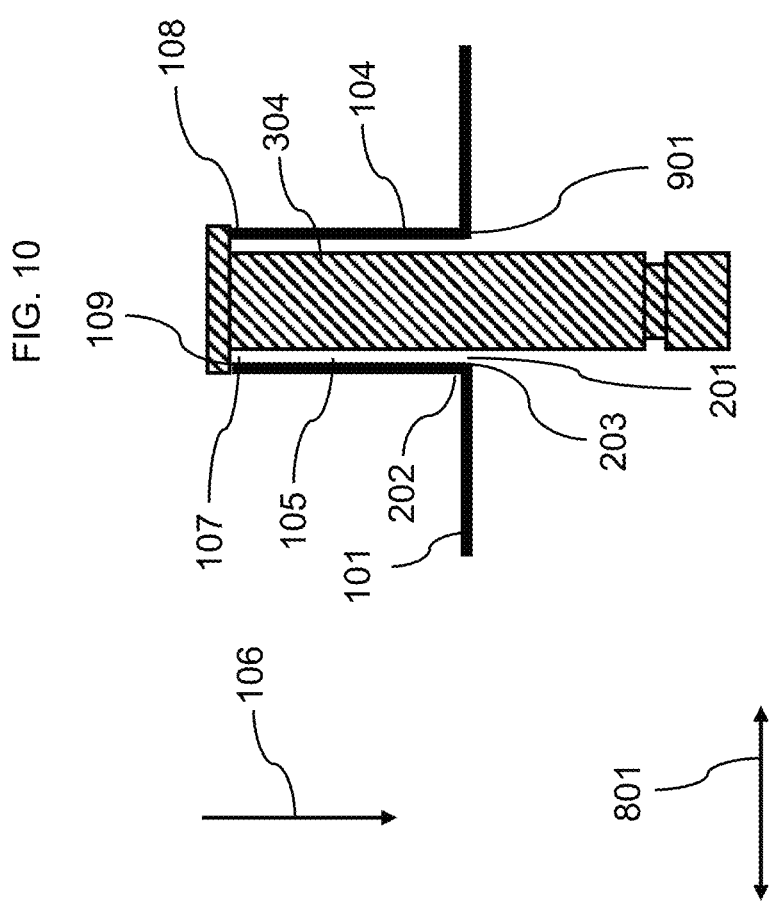

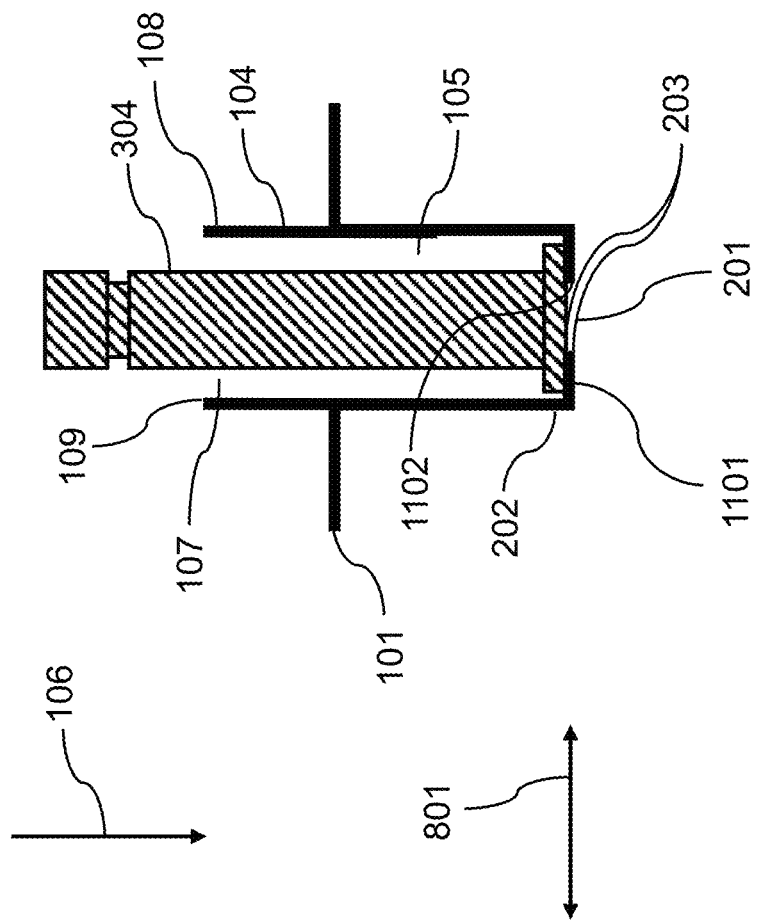

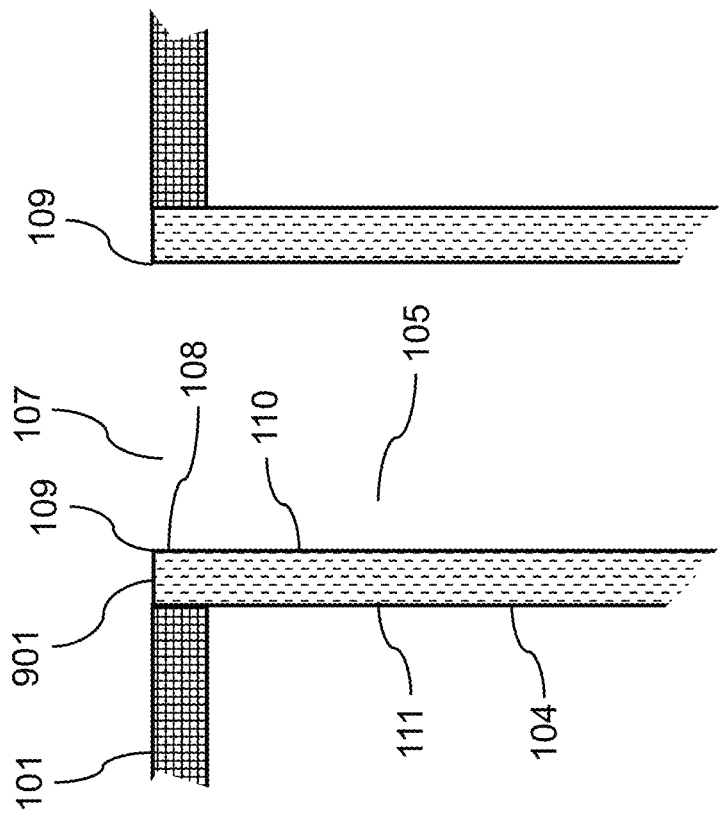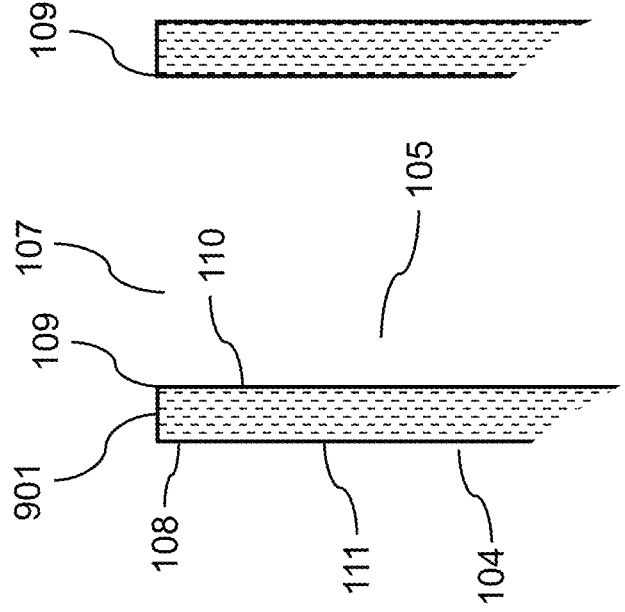

1500

500 μm

HOLDING DEVICE HAVING A TOTAL HEIGHT $R_t$ OF A ROUGHNESS PROFILE

CROSS REFERENCE TO RELATED APPLICATIONS

This claims priority to European patent application no. EP 22154057.8, entitled "HOLDING DEVICE HAVING A TOTAL HEIGHT $R_t$ OF A ROUGHNESS PROFILE", filed Jan. 28, 2022, which is incorporated herein by reference.

BACKGROUND OF THE INVENTION

1. Field of the Invention

The present invention relates to pharmaceutical packaging, and, more particularly, to holding devices for holding primary packaging containers for pharmaceutical, medical, or cosmetic compositions.

2. Description of the Related Art

Containers made from glass and later on also from polymer have been applied for transporting fluids and powders safely for a long time. In the last decades, the arts in which glass and polymer containers are used for transporting fluids and powders have become increasingly diverse and sophisticated. One such art is the technical field of the present application: pharmaceutical packaging. In the pharmaceutical industry, containers—such as vials, syringes, ampoules and cartridges—are used as primary packaging for all kinds of pharmaceutically relevant compositions, in particular drugs, such as vaccines, and also for cosmetical compositions, in particular cosmetical compositions which are to be injected into the skin.

In the processing of containers for use in pharmaceutical or cosmetical applications, generally so-called nested solutions are preferred nowadays, where a holding structure for containers (also referred to as nest) is used for concurrently holding or supporting a plurality of primary packaging containers in a given configuration. An example of a known nested solution is commercially available from Schott AG under the tradename SCHOTT iQ© platform. The nest with the primary packaging containers is usually delivered to a customer, such as a pharmaceutical company or filler, packaged in a transport or packaging container (also referred to as tub). For further processing the primary packaging containers, the tub is opened. Further processing of the primary packaging containers often includes automated steps of removing the primary packaging containers from the tub; filling the primary packaging containers with a composition, e.g. a pharmaceutical or cosmetical composition; and closing the pre-filled primary packaging containers.

The above-described known nests are produced by injection molding. Therein, the mold includes top and bottom parts. Generally, during molding, polymer melt can get into the gap of microscopic but finite width between the mold parts. This polymer melt will form burrs on the demolded nest.

Further, upon separating the mold parts after forming the nest, the latter, due to its shrinkage, adheres to the upper, horizontally aligned part of the mold. A multitude of pushers, often pins, is used to detach the nest from the horizontally aligned mold part which it adheres to. Those pushers are distributed across the whole length and width of the nest in order for the nest to be pushed from the mold part in an as horizontal as possible alignment. The higher the angle, which the nest forms with the horizontal plane during its downwards movement, the higher is the risk of stress marks and scratches to the nest. As the multiple pushers have to attack the nest from above through the mold part, the latter has openings, through which the pushers can reach the nest. In order for it be possible to move the pushers forward and backwards, there is a minimum gap between the pushers and the mold part. When polymer melt gets into these gaps, further burrs on the nest result.

In addition, the mold has small exhaust openings for the air from the mold interior to be released upon injecting the polymer melt into the mold. Without such openings, the air in the mold would be compressed to a very high degree until it is very hot and is released in an explosive manner. If that happens, the nest may be burned. Thus, exhaust openings for the air to be released from the mold are needed. Of course, these openings are a further source for burrs on the nest.

The above technical requirement of producing the nests of the so-called nested solutions of pharmaceutical and cosmetic packaging shows that, without counter-measures being taken, the nests will have burrs. Post-treatment of the nests for deburring has been expected to be a major source of macroscopic and microscopic particles. If such particles are generated from the nest material, they will adhere to the primary packaging containers which are held in the nest. On the exterior surfaces of the primary packaging containers, such particles can hamper optical inspection of the containers for quality control. Even more severe is the risk of such particles getting into the primary packaging containers, for example on a filling line, on which the containers are filled with a pharmaceutical or cosmetic composition. In the worst case, particles could end up being injected into a patient. Needless to say, this has to be avoided strictly. Therefore, a deburring post-treatment to the nests has been refrained from in the prior art. Studies, which the present invention originated from, however, surprisingly revealed that reducing the total height $R_t$ of roughness profiles on very specific sites of the nests, in particular of their receptacles, for example by a deburring post-treatment of these specific sites, results in a reduction of particle generation upon handling and transporting the nests which outweighs the particle generation caused by the post-treatment itself.

In general, what is needed in the art is to at least partly overcome a disadvantage arising from the prior art.

What is also needed in the art is a nested solution of pharmaceutical, medical or cosmetic packaging which improves patient safety. What is also needed in the art is a nested solution of pharmaceutical, medical or cosmetic packaging which allows to reduce a particle load on the nested primary packaging containers after having been transported in the nest. What is also needed in the art is a nested solution of pharmaceutical, medical or cosmetic packaging which improves quality control, in particular by optical inspection, of the nested primary packaging containers.

SUMMARY OF THE INVENTION

A contribution to at least partly fulfilling at least one, optionally more than one, of the above-mentioned needs is made by any of the embodiments of the invention. The present invention refers to a holding device for holding a plurality of primary packaging containers for pharmaceutical, medical or cosmetic compositions, the holding device including
  a plate-shaped carrier element which includes a plurality of through-holes, and a plurality of receptacles, each of which is designed and arranged to accommodate one of the primary packaging containers;
wherein each of the receptacles includes a receptacle wall which partially encloses a receptacle interior; wherein each receptacle wall forms a wall body; wherein each wall body extends in a longitudinal direction through one of the through-holes of the plurality of through-holes, and
has a first opening at a first end and a further opening at a further end which, in the longitudinal direction, is opposite to the first end;
wherein the first opening of each wall body is laterally directly surrounded by at least one first edge of the respective wall body; wherein the further opening of each wall body is laterally directly surrounded by at least one further edge of the respective wall body; characterized by at least 50% of the receptacles of the plurality of receptacles having a total height $R_t$ of a roughness profile of
the at least one first edge, or
the at least one further edge, or
each of both
of not more than 0.50 mm. The invention further pertains to a further holding device, a process of producing one of the preceding holding devices, an arrangement and a transport unit, in each case including one of the preceding holding devices, and to uses of one of the preceding holding devices.

A $1^{st}$ embodiment of the invention is a holding device for holding a plurality of primary packaging containers for pharmaceutical, medical or cosmetic compositions, the holding device including
a plate-shaped carrier element which includes a plurality of through-holes, and
a plurality of receptacles, each of which is designed and arranged to accommodate one of the primary packaging containers;
wherein each of the receptacles includes a receptacle wall which partially encloses a receptacle interior; wherein each receptacle wall forms a wall body; wherein each wall body extends in a longitudinal direction through one of the through-holes of the plurality of through-holes, and
has a first opening at a first end and a further opening at a further end which, in the longitudinal direction, is opposite to the first end;
wherein the first opening of each wall body is laterally directly surrounded by at least one first edge, optionally at least two first edges, optionally exactly two first edges, of the respective wall body; wherein the further opening of each wall body is laterally directly surrounded by at least one further edge, optionally two further edges, optionally exactly two further edges, of the respective wall body; characterized by at least 50%, optionally at least 60%, optionally at least 70%, optionally at least 80%, optionally at least 90%, optionally at least 95%, optionally at least 98%, optionally 100%, of the receptacles of the plurality of receptacles having a total height $R_t$ of a roughness profile of
the at least one first edge, or
the at least one further edge, or
each of both
of not more than 0.50 mm, optionally not more than 0.45 mm, optionally not more than 0.40 mm, optionally not more than 0.35 mm, optionally not more than 0.30 mm, optionally not more than 0.25 mm, optionally not more than 0.20 mm, optionally not more than 0.15 mm, optionally not more than 0.14 mm, optionally not more than 0.13 mm, optionally not more than 0.12 mm, optionally not more than 0.11 mm, optionally not more than 0.10 mm, optionally not more than 0.09 mm, optionally not more than 0.08 mm, optionally not more than 0.07 mm, optionally not more than 0.06 mm, optionally not more than 0.05 mm, optionally not more than 0.04 mm, optionally not more than 0.03 mm, optionally not more than 0.02 mm, optionally not more than 0.01 mm, optionally not more than 0.009 mm, optionally not more than 0.008 mm, optionally not more than 0.007 mm, optionally not more than 0.006 mm, optionally not more than 0.005 mm.

In an optional embodiment of the holding device, for each of the receptacles of the plurality of receptacles, the wall body has
an interior surface which faces the receptacle interior, and
an exterior surface which faces opposite to the interior surface.
This optional embodiment is a $2^{nd}$ embodiment of the invention, that optionally depends on the $1^{st}$ embodiment of the invention.

In an optional embodiment of the holding device, at least 50%, optionally at least 60%, optionally at least 70%, optionally at least 80%, optionally at least 90%, optionally at least 95%, optionally at least 98%, optionally 100%, of the receptacles of the plurality of receptacles have a maximum total height $R_t$ of roughness profiles of the interior surface of not more than 0.50 mm, optionally not more than 0.45 mm, optionally not more than 0.40 mm, optionally not more than 0.35 mm, optionally not more than 0.30 mm, optionally not more than 0.25 mm, optionally not more than 0.20 mm, optionally not more than 0.15 mm, optionally not more than 0.14 mm, optionally not more than 0.13 mm, optionally not more than 0.12 mm, optionally not more than 0.11 mm, optionally not more than 0.10 mm, optionally not more than 0.09 mm, optionally not more than 0.08 mm, optionally not more than 0.07 mm, optionally not more than 0.06 mm, optionally not more than 0.05 mm, optionally not more than 0.04 mm, optionally not more than 0.03 mm, optionally not more than 0.02 mm, optionally not more than 0.01 mm, optionally not more than 0.009 mm, optionally not more than 0.008 mm, optionally not more than 0.007 mm, optionally not more than 0.006 mm, optionally not more than 0.005 mm. This optional embodiment is a $3^{rd}$ embodiment of the invention, that optionally depends on the $2^{nd}$ embodiment of the invention.

A $4^{th}$ embodiment of the invention is a holding device for holding a plurality of primary packaging containers for pharmaceutical, medical or cosmetic compositions, the holding device including
a plate-shaped carrier element which includes a plurality of through-holes, and
a plurality of receptacles, each of which is designed and arranged to accommodate one of the primary packaging containers;
wherein each of the receptacles includes a receptacle wall which partially encloses a receptacle interior; wherein each receptacle wall forms a wall body; wherein each wall body extends in a longitudinal direction through one of the through-holes of the plurality of through-holes; wherein, for each of the receptacles of the plurality of receptacles, the wall body has
an interior surface which faces the receptacle interior, and
an exterior surface which faces opposite to the interior surface;
characterized by at least 50%, optionally at least 60%, optionally at least 70%, optionally at least 80%, optionally at least 90%, optionally at least 95%, optionally at least 98%, optionally 100%, of the receptacles of the plurality of receptacles having a maximum total height $R_t$ of roughness profiles of the interior surface of not more than 0.50 mm, optionally not more than 0.45 mm, optionally not more than 0.40 mm, optionally not more than 0.35 mm, optionally not more than 0.30 mm, optionally not more than 0.25 mm, optionally not more than 0.20 mm, optionally not more than 0.15 mm, optionally not more than 0.14 mm, optionally not more than 0.13 mm, optionally not more than 0.12 mm, optionally not more than 0.11 mm, optionally not more than 0.10 mm, optionally not more than 0.09 mm, optionally not more than 0.08 mm, optionally not more than 0.07 mm, optionally not more than 0.06 mm, optionally not more than 0.05 mm, optionally not more than 0.04 mm, optionally not more than 0.03 mm, optionally not more than 0.02 mm, optionally not more than 0.01 mm, optionally not more than 0.009 mm, optionally not more than 0.008 mm, optionally not more than 0.007 mm, optionally not more than 0.006 mm, optionally not more than 0.005 mm.

In an optional embodiment of the holding device, each wall body has a first opening at a first end and a further opening at a further end which, in the longitudinal direction, is opposite to the first end; wherein the first opening of each wall body is laterally directly surrounded by at least one first edge, optionally at least two first edges, optionally exactly two first edges, of the respective wall body; wherein the further opening of each wall body is laterally directly surrounded by at least one further edge, optionally at least two further edges, optionally exactly two further edges, of the respective wall body. This optional embodiment is a 5$^{th}$ embodiment of the invention, that optionally depends on the 4$^{th}$ embodiment of the invention.

In an optional embodiment of the holding device, at least 50%, optionally at least 60%, optionally at least 70%, optionally at least 80%, optionally at least 90%, optionally at least 95%, optionally at least 98%, optionally 100%, of the receptacles of the plurality of receptacles have a total height $R_t$ of a roughness profile of
the at least one first edge, or
the at least one further edge, or
each of both
of not more than 0.50 mm, optionally not more than 0.45 mm, optionally not more than 0.40 mm, optionally not more than 0.35 mm, optionally not more than 0.30 mm, optionally not more than 0.25 mm, optionally not more than 0.20 mm, optionally not more than 0.15 mm, optionally not more than 0.14 mm, optionally not more than 0.13 mm, optionally not more than 0.12 mm, optionally not more than 0.11 mm, optionally not more than 0.10 mm, optionally not more than 0.09 mm, optionally not more than 0.08 mm, optionally not more than 0.07 mm, optionally not more than 0.06 mm, optionally not more than 0.05 mm, optionally not more than 0.04 mm, optionally not more than 0.03 mm, optionally not more than 0.02 mm, optionally not more than 0.01 mm, optionally not more than 0.009 mm, optionally not more than 0.008 mm, optionally not more than 0.007 mm, optionally not more than 0.006 mm, optionally not more than 0.005 mm. This optional embodiment is a 6$^{th}$ embodiment of the invention, that optionally depends on the 5$^{th}$ embodiment of the invention.

In an optional embodiment of the holding device, for each of the receptacles of the plurality of receptacles, the wall body includes a retaining part which
extends laterally,
limits the receptacle interior in the longitudinal direction or in a counter direction of the longitudinal direction, and
includes the first opening or the further opening.

This optional embodiment is a 7$^{th}$ embodiment of the invention, that optionally depends on any of the 1$^{st}$ to 3$^{rd}$, 5$^{th}$ and 6$^{th}$ embodiments of the invention.

The retaining part is, optionally, designed and arranged to support one of the primary packaging containers of the plurality of primary packaging containers, optionally against gravity when the holding device is upright, when being accommodated in the respective receptacle. Optionally, the retaining part is designed and arranged to keep a primary packaging container, which is accommodated in the respective receptacle, from falling through the receptacle in the direction of gravity when the holding device is upright.

In an optional embodiment of the holding device, for each of the receptacles of the plurality of receptacles, the first opening or the further opening is laterally limited by a lateral surface of the retaining part, wherein at least 50%, optionally at least 60%, optionally at least 70%, optionally at least 80%, optionally at least 90%, optionally at least 95%, optionally at least 98%, optionally 100%, of the receptacles of the plurality of receptacles have a maximum total height $R_t$ of roughness profiles of the lateral surface of the retaining part of not more than 0.50 mm, optionally not more than 0.45 mm, optionally not more than 0.40 mm, optionally not more than 0.35 mm, optionally not more than 0.30 mm, optionally not more than 0.25 mm, optionally not more than 0.20 mm, optionally not more than 0.15 mm, optionally not more than 0.14 mm, optionally not more than 0.13 mm, optionally not more than 0.12 mm, optionally not more than 0.11 mm, optionally not more than 0.10 mm, optionally not more than 0.09 mm, optionally not more than 0.08 mm, optionally not more than 0.07 mm, optionally not more than 0.06 mm, optionally not more than 0.05 mm, optionally not more than 0.04 mm, optionally not more than 0.03 mm, optionally not more than 0.02 mm, more optionally not more than 0.01 mm, more optionally not more than 0.009 mm, optionally not more than 0.008 mm, optionally not more than 0.007 mm, optionally not more than 0.006 mm, optionally not more than 0.005 mm. This optional embodiment is an 8$^{th}$ embodiment of the invention, that optionally depends on the 7$^{th}$ embodiment of the invention.

In an optional embodiment of the holding device, for each of the receptacles of the plurality of receptacles, the wall body further has at least one intermediate surface which
is neither part of the interior surface nor of the exterior surface, and
faces in the longitudinal direction or in a counter direction of the longitudinal direction,
wherein at least 50%, optionally at least 60%, optionally at least 70%, optionally at least 80%, optionally at least 90%, optionally at least 95%, optionally at least 98%, optionally 100%, of the receptacles of the plurality of receptacles have a maximum total height $R_t$ of roughness profiles of the at least one intermediate surface of not more than 0.50 mm, optionally not more than 0.45 mm, optionally not more than 0.40 mm, optionally not more than 0.35 mm, optionally not more than 0.30 mm, optionally not more than 0.25 mm, optionally not more than 0.20 mm, optionally not more than 0.15 mm, optionally not more than 0.14 mm, optionally not more than 0.13 mm, optionally not more than 0.12 mm, optionally not more than 0.11 mm, optionally not more than 0.10 mm, optionally not more than 0.09 mm, optionally not more than 0.08 mm, optionally not more than 0.07 mm, optionally not more than 0.06 mm, optionally not more than 0.05 mm, optionally not more than 0.04 mm, optionally not more than 0.03 mm, optionally not more than 0.02 mm, optionally not more than 0.01 mm, optionally not more than 0.009 mm, optionally not more than 0.008 mm, optionally not more than 0.007 mm, optionally not more than 0.006 mm, optionally not more than 0.005 mm. This optional embodiment is a $9^{th}$ embodiment of the invention, that optionally depends on any of the $2^{nd}$ to $8^{th}$ embodiments of the invention.

In an optional embodiment of the holding device, the at least one intermediate surface is adjacent to the interior surface, the exterior surface, or each of both. This optional embodiment is a $10^{th}$ embodiment of the invention, that optionally depends on the $9^{th}$ embodiment of the invention.

In an optional embodiment of the holding device, the at least one intermediate surface is adjacent to the interior surface, but not to the exterior surface. This optional embodiment is a $11^{th}$ embodiment of the invention, that optionally depends on the $9^{th}$ embodiment of the invention.

Optionally, part of the plate-shaped carrier element is between the exterior surface and the intermediate surface.

In an optional embodiment of the holding device, for each of the receptacles of the plurality of receptacles, an opening area of the first opening is larger than an opening area of the further opening, optionally by at least 5%, optionally at least 10%, optionally at least 20%, optionally at least 30%, in each case based on the opening area of the further opening. This optional embodiment is a $12^{th}$ embodiment of the invention, that optionally depends on any of the $1^{st}$ to $3^{rd}$ and $5^{th}$ to $11^{th}$ embodiments of the invention.

In an optional embodiment of the holding device, for each of the receptacles of the plurality of receptacles, the first opening is closer to the plate-shaped carrier element than the further opening. This optional embodiment is a $13^{th}$ embodiment of the invention, that optionally depends on any of the $1^{st}$ to $3^{rd}$ and $5^{th}$ to $12^{th}$ embodiments of the invention.

In an optional embodiment of the holding device, for each of the receptacles of the plurality of receptacles, the first edge or the further edge is laterally surrounded by the plate-shaped carrier element. This optional embodiment is a $14^{th}$ embodiment of the invention, that optionally depends on any of the $1^{st}$ to $3^{rd}$ and $5^{th}$ to $13^{th}$ embodiments of the invention.

In an optional embodiment of the holding device, for each of the receptacles of the plurality of receptacles, the first end or the further end or each of both protrudes from the plate-shaped carrier element in the longitudinal direction or in a counter direction of the longitudinal direction. This optional embodiment is a $15^{th}$ embodiment of the invention, that optionally depends on any of the $1^{st}$ to $3^{rd}$ and $5^{th}$ to $14^{th}$ embodiments of the invention.

In an optional embodiment of the holding device, for each of the receptacles of the plurality of receptacles, the first end or the further end is directly connected to the plate-shaped carrier element. This optional embodiment is a $16^{th}$ embodiment of the invention, that optionally depends on any of the $1^{st}$ to $3^{rd}$ and $5^{th}$ to $15^{th}$ embodiments of the invention.

Optionally, at the first end or the further end, the exterior surface of the wall body of the respective receptacle is directly connected to the plate-shaped carrier element.

In an optional embodiment of the holding device, the plate-shaped carrier element is in one piece with each of the wall bodies. This optional embodiment is a $17^{th}$ embodiment of the invention, that optionally depends on any of the preceding embodiments of the invention.

Optionally, the wall bodies have been made from a polymer composition, optionally by a molding process. Further optionally, the plate-shaped carrier element has been made from the polymer composition, optionally by the molding process. An optional molding process is an injection molding process. An optional polymer composition is thermoplastic.

In an optional embodiment of the holding device, the holding device is designed to, optionally non-destructively, detachably accommodate a primary packaging container of the plurality of primary packaging containers in each of the receptacles of the plurality of receptacles. Optionally, the holding device is designed to hold the primary packaging containers in the receptacles by a form-fit or a force-fit or both. This optional embodiment is an $18^{th}$ embodiment of the invention, that optionally depends on any of the preceding embodiments of the invention.

In an optional embodiment of the holding device, the plurality of receptacles includes a number of receptacles which is in the range from 4 to 500, optionally from 9 to 400, optionally from 12 to 300, optionally from 16 to 200, optionally from 16 to 160, optionally from 16 to 100, optionally from 16 to 90, optionally from 16 to 80, optionally from 16 to 70, optionally from 16 to 60, optionally from 16 to 50. This optional embodiment is a $19^{th}$ embodiment of the invention, that optionally depends on any of the preceding embodiments of the invention.

In an optional embodiment of the holding device, the primary packaging containers of the plurality of primary packaging containers are selected from the group consisting of vials, syringes, cartridges, and ampoules, or a combination of at least two thereof. An optional cartridge is designed for being used as a reservoir in a, optionally portable, medical device. An optional portable medical device is an insulin pump. This optional embodiment is a $20^{th}$ embodiment of the invention, that optionally depends on any of the preceding embodiments of the invention.

A $21^{st}$ embodiment of the invention is a process of producing the holding device according to any of the preceding claims, the process including process steps of:
  a) providing
    i) a first part of a mold, and
    ii) a further part of the mold;
  b) positioning the first part and the further part relative to one another such that the first part and the further part together at least partially enclose an interior of the mold;
  c) introducing a polymer composition into the interior of the mold;
  d) solidifying the polymer composition in the interior of the mold, thereby obtaining a molded body; and
  e) demolding the molded body.

In an optional embodiment of the process, in the process step c), the polymer composition is liquid or granular. An optional liquid polymer composition is a polymer melt. This optional embodiment is a $22^{nd}$ embodiment of the invention, that optionally depends on the $21^{st}$ embodiment of the invention.

In an optional embodiment of the process, the process is an injection molding process. This optional embodiment is a $23^{rd}$ embodiment of the invention, that optionally depends on the $21^{st}$ or $22^{nd}$ embodiment of the invention.

In an optional embodiment of the process, the molded body which is demolded in the process step e) is the holding device. This optional embodiment is a $24^{th}$ embodiment of the invention, that optionally depends on any of the $21^{st}$ to $23^{rd}$ embodiments of the invention.

In an optional embodiment of the process, the process includes a further process step which includes a treatment of the molded body, wherein the holding device is obtained from the molded body by the treatment. This optional embodiment is a 25$^{th}$ embodiment of the invention, that optionally depends on any of the 21$^{st}$ to 23$^{rd}$ embodiments of the invention.

In an optional embodiment of the process, the treatment is a mechanical treatment, or a thermal treatment, or both. An optional thermal treatment includes heating at least part of the molded body. Optionally, heating is effected by irradiation with electromagnetic radiation. An optional electromagnetic radiation is infrared radiation. This optional embodiment is a 26$^{th}$ embodiment of the invention, that optionally depends on the 25$^{th}$ embodiment of the invention.

In an optional embodiment of the process, the further process step is carried out before the process step e), or after the process step e), or both. This optional embodiment is a 27$^{th}$ embodiment of the invention, that optionally depends on the 25$^{th}$ or 26$^{th}$ embodiment of the invention.

In an optional embodiment of the process, the process step e) includes sub-steps of
  i) removing the first part from the molded body, and
  ii) pushing the molded body from the further part by applying a demolding force to the molded body.

This optional embodiment is a 28$^{th}$ embodiment of the invention, that optionally depends on any of the 21$^{st}$ to 27$^{th}$ embodiments of the invention.

In an optional embodiment of the process, the demolding force is directed in the longitudinal direction. This optional embodiment is a 29$^{th}$ embodiment of the invention, that optionally depends on the 28$^{th}$ embodiment of the invention.

In an optional embodiment of the process, the demolding force is applied by a plurality of demolding elements. An optional demolding element is a pin or a bolt or both. This optional embodiment is a 30$^{th}$ embodiment of the invention, that optionally depends on the 28$^{th}$ or 29$^{th}$ embodiment of the invention.

In an optional embodiment of the process, the molded body includes the plate-shaped carrier element, wherein sites of application of the demolding force are distributed across a lateral extension of the plate-shaped carrier element such that an angle which the plate-shaped carrier element forms with a horizontal plane does not exceed 20°, optionally 10°, optionally 5°, optionally 3°, in the process step e). Here, the lateral extension of the plate-shaped carrier element refers to its width and length. This optional embodiment is a 31$^{st}$ embodiment of the invention, that optionally depends on any of the 28$^{th}$ to 30$^{th}$ embodiments of the invention.

A 32$^{nd}$ embodiment of the invention is a holding device which is obtainable by the process of to the invention, optionally according to the 21$^{st}$ to 31$^{st}$ embodiments of the invention.

A 33$^{rd}$ embodiment of the invention is an arrangement including
  the holding device of to the invention, optionally according to any of the 1$^{st}$ to 20$^{th}$, or 32$^{nd}$ embodiments of the invention, and
  the plurality of primary packaging containers,
wherein each of the primary packaging containers is accommodated in one of the receptacles. Optionally, each of the primary packaging containers is, optionally non-destructively, detachably accommodated in one of the receptacles.

In an optional embodiment of the arrangement, the plurality of primary packaging containers includes a number of primary packaging containers which is in the range from 4 to 500, optionally from 9 to 400, optionally from 12 to 300, optionally from 16 to 200, optionally from 16 to 160, optionally from 16 to 100, optionally from 16 to 90, optionally from 16 to 80, optionally from 16 to 70, optionally from 16 to 60, optionally from 16 to 50. This optional embodiment is a 34$^{th}$ embodiment of the invention, that optionally depends on the 33$^{rd}$ embodiment of the invention.

In an optional embodiment of the arrangement, each of the primary packaging containers contains a pharmaceutical, medical or cosmetic composition. This optional embodiment is a 35$^{th}$ embodiment of the invention, that optionally depends on the 33$^{rd}$ or 34$^{th}$ embodiment of the invention.

In an optional embodiment of the arrangement, each of the primary packaging containers is closed. This optional embodiment is a 36$^{th}$ embodiment of the invention, that optionally depends on any of the 33$^{rd}$ to 37$^{th}$ embodiments of the invention.

In an optional embodiment of the arrangement, each of the primary packaging containers includes, in the following sequence along its length,
  a) a first end part, including a discharge opening,
  b) a body part, and
  c) a further end part.

This optional embodiment is a 37$^{th}$ embodiment of the invention, that optionally depends on any of the 33$^{rd}$ to 36$^{th}$ embodiments of the invention.

In an optional embodiment of the arrangement, the body part is of cylindrical shape. This optional embodiment is a 38$^{th}$ embodiment of the invention, that optionally depends on the 37$^{th}$ embodiment of the invention.

In an optional embodiment of the arrangement, the further end part is a standing base, or includes a further opening, or both. An optional further orifice is designed to accommodate a plunger. This optional embodiment is a 39$^{th}$ embodiment of the invention, that optionally depends on the 37$^{th}$ or 38$^{th}$ embodiment of the invention.

In an optional embodiment of the arrangement, for each of the primary packaging containers, an area of the further opening is more than an area of the discharge opening. This optional embodiment is a 40$^{th}$ embodiment of the invention, that optionally depends on the 39$^{th}$ embodiment of the invention.

In an optional embodiment of the arrangement, the further end part further includes a rim which projects laterally from the body part and at least partially, optionally fully, hems the further opening. This optional embodiment is a 41$^{st}$ embodiment of the invention, that optionally depends on the 39$^{th}$ or 40$^{th}$ embodiments of the invention.

In an optional embodiment of the arrangement, the first end part of each of the primary packaging containers includes a connecting element, wherein the connecting element includes a thread for connecting an auxiliary part to the primary packaging container. An optional auxiliary part is one selected from the group consisting of a needle, a nozzle, and a tubing, or a combination of at least two therefore. An optional needle is a hypodermic needle. This optional embodiment is a 42$^{nd}$ embodiment of the invention, that optionally depends on any of the 37$^{th}$ to 41$^{st}$ embodiments of the invention.

In an optional embodiment of the arrangement, the connecting element includes a thread for connecting an auxiliary part to the respective primary packaging container. This optional embodiment is a 43$^{rd}$ embodiment of the invention, that optionally depends on the 42$^{nd}$ embodiment of the invention.

In an optional embodiment of the arrangement, the first end part of each of the primary packaging containers includes a male part of a taper fitting. An optional taper fitting is a Luer taper. Generally, the Luer taper may include a thread or not. This optional embodiment is a 44$^{th}$ embodiment of the invention, that optionally depends on any of the 37th to 43rd embodiments of the invention.

In an optional embodiment of the arrangement, the male part of the taper fitting includes a thread. Optionally, the thread is arranged in a sleeve. This optional embodiment is a 45th embodiment of the invention, that optionally depends on the 44th embodiment of the invention.

In an optional embodiment of the arrangement, for each of the primary packaging containers, throughout the body part a thickness of a container wall is in a range from ±0.3 mm, optionally ±0.2 mm, optionally ±0.15 mm, optionally ±0.1 mm, optionally ±0.08 mm, in each case based on a mean value of the thickness of the container wall in the body part of the respective primary packaging container. This optional embodiment is a 46th embodiment of the invention, that optionally depends on any of the 37th to 45th embodiments of the invention.

In an optional embodiment of the arrangement, for each of the primary packaging containers, throughout the body part a thickness of a container wall is in a range from 0.2 to 3 mm, optionally from 0.3 to 2.5 mm, optionally from 0.4 to 2.2 mm. This optional embodiment is a 47th embodiment of the invention, that optionally depends on any of the 37th to 46th embodiments of the invention.

In an optional embodiment, for each of the primary packaging containers, throughout the body part a thickness of a container wall is in a range from 1.0 to 1.1 mm. In a further optional embodiment, for each of the primary packaging containers, throughout the body part a thickness of a container wall is in a range from 1.4 to 1.8 mm. In yet a further optional embodiment, for each of the primary packaging containers, throughout the body part a thickness of a container wall is in a range from 0.6 to 2.0 mm.

In an optional embodiment of the arrangement, each of the primary packaging containers has a container interior with a volume in a range from 0.5 to 100 ml, optionally from 1 to 100 ml, optionally from 1 to 50 ml, optionally from 1 to 10 ml, optionally from 2 to 10 ml. This optional embodiment is a 48th embodiment of the invention, that optionally depends on any of the 33rd to 47th embodiments of the invention.

In an optional embodiment of the arrangement, the primary packaging containers are selected from the group consisting of vials, syringes, cartridges, and ampoules, or a combination of at least two thereof. An optional cartridge is designed for being used as a reservoir in a, optionally portable, medical device. An optional portable medical device is an insulin pump. This optional embodiment is a 49th embodiment of the invention, that optionally depends on any of the 33rd to 48th embodiments of the invention.

In an optional embodiment of the arrangement, each of the primary packaging containers includes a container wall which at least partially surrounds a container interior, wherein the container wall includes, optionally consists of, a glass, or a polymer, or both. This optional embodiment is a 50th embodiment of the invention, that optionally depends on any of the 33rd to 49th embodiments of the invention.

In an optional embodiment of the arrangement, the polymer is a cyclic olefin copolymer, or a cycloolefin polymer, or a mixture thereof. This optional embodiment is a 51st embodiment of the invention, that optionally depends on the 50th embodiment of the invention.

In an optional embodiment of the arrangement, the glass is of a type selected from the group consisting of a borosilicate glass, optionally a type I glass; an aluminosilicate glass; and fused silica; or of a combination of at least two thereof. This optional embodiment is a 52nd embodiment of the invention, that optionally depends on the 50th or 51st embodiment of the invention.

In an optional embodiment of the arrangement, the primary packaging containers have been decontaminated, optionally sterilized. This optional embodiment is a 53rd embodiment of the invention, that optionally depends on any of the 33rd to 52nd embodiments of the invention.

Optionally, the arrangement has been decontaminated, optionally sterilized. In the context of the present application, decontamination is defined as an umbrella term for reducing the amount of microbes and biological agents, such as fungi, bacteria, viruses, spore forms, prions, unicellular eukaryotic organisms, etc. The special terms disinfection and sterilization differ in the amount of reduction of these. While disinfection only reduces the amount of said contaminants, sterilization effectively kills, deactivates, or eliminates all forms of life and other biological agents which are present, i.e., a reduction of 100%. Hence, disinfection is less effective than sterilization.

A 54th embodiment of the invention is a transport unit including
 the arrangement of the invention, optionally according to any of the 33rd to 53rd embodiments of the invention, and
 a secondary packaging container,
wherein the holding device and the plurality of primary packaging containers arranged completely in the secondary packaging container.

In an optional embodiment of the transport unit, a container body of the secondary packaging container includes
 a container opening, and
 a container base which is opposite to the container opening in the longitudinal direction.

This optional embodiment is a 55th embodiment of the invention, that optionally depends on the 54th embodiment of the invention.

In an optional embodiment of the transport unit, the first end parts, or the further end parts of the primary packaging containers face the container opening. This optional embodiment is a 56th embodiment of the invention, that optionally depends on the 55th embodiment of the invention.

In an optional embodiment of the transport unit, the secondary packaging container is a tub or tub-shaped. This optional embodiment is a 57th embodiment of the invention, that optionally depends on any of the 54th to 56th embodiments of the invention.

In an optional embodiment of the transport unit, the secondary packaging container is closed by a lid. Optionally, the lid is joined to the secondary packaging container. An optional lid is a multi-layer sheet. Additionally or alternatively optional, the lid is gas-permeable. This optional embodiment is a 58th embodiment of the invention, that optionally depends on any of the 54th to 57th embodiments of the invention.

In an optional embodiment of the transport unit, the transport unit further includes an, optionally closed, outer packaging, wherein the secondary packaging container is arranged in the outer packaging. This optional embodiment is a 59th embodiment of the invention, that optionally depends on any of the 54th to 58th embodiments of the invention.

An optional outer packaging is a pouch, optionally made from a plastic film. Additionally or alternatively optional, the outer packaging provides a barrier against a permeation of an inert gas. Additionally or alternatively optional, the outer packaging is hermetically sealed. Additionally or alternatively optional, the outer packaging is less permeable for the inert gas than the lid. Particularly optional the outer packing provides a barrier action against a permeation of the inert gas, whereas the lid is permeable for the inert gas.

In an optional embodiment of the transport unit, the outer packaging includes an atmosphere which includes an inert gas at a proportion of at least 50 vol.-%, optionally at least 60 vol.-%, optionally at least 70 vol.-%, optionally at least 80 vol.-%, optionally at least 90 vol.-%, optionally at least 95 vol.-%, in each case based on a volume of the atmosphere. This optional embodiment is a $60^{th}$ embodiment of the invention, that optionally depends on the $59^{th}$ embodiment of the invention.

A $61^{st}$ embodiment of the invention is a use of the holding device of the invention, optionally according to any of the $1^{st}$ to $20^{th}$, or $32^{nd}$ embodiments of the invention, or of the arrangement of the invention, optionally according to any of the $33^{rd}$ to $53^{rd}$ embodiments of the invention, or of the transport unit of the invention, optionally according to any of the $48^{th}$ to $54^{th}$ embodiments of the invention, in each case for storing or transporting the plurality of primary packaging containers.

In an optional embodiment of the use, each of the primary packaging containers contains a pharmaceutical, medical or cosmetic composition. This optional embodiment is a $62^{nd}$ embodiment of the invention, that optionally depends on the $61^{st}$ embodiment of the invention.

A $63^{rd}$ embodiment of the invention is a use of the holding device of the invention, optionally according to any of the $1^{st}$ to $20^{th}$, or $32^{nd}$ embodiments of the invention, for holding the plurality of primary packaging containers in a step of filling the primary packaging containers with a pharmaceutical, medical or cosmetic composition.

Features described as optional in one category of the invention, for example according to the holding device, are analogously optional in an embodiment of the other categories according to the invention, such as the process, the arrangement, the transport unit and the uses.

Holding Device

The holding device of the invention may, generally, be any device which, for the skilled person, comes into consideration for holding the plurality of primary packaging containers. An optional holding device is a carrier structure of a so-called nested solution as they are generally known in the technical field of transport packaging for medical, pharmaceutical and cosmetical primary packaging containers. An example of a known nested solution is commercially available from Schott AG under the tradename SCHOTT iQ® platform. An optional holding device has been prepared by deep drawing or injection molding, where injection molding is particularly optional. Additionally or alternatively optional, the holding device is made from one or more plastics. Optionally, the plate-shaped carrier element is in one piece with the plurality of receptacles. Further optionally, the holding device is of a one-piece design. Optionally, the receptacles form a regular pattern in a top view on the holding device.

Plate-Shaped Carrier Element

The term "plate-shaped" refers to a width and a length of the carrier element each being at least 5 times, optionally at least 10 times, optionally at least 50 times, optionally at least 100 times, more than a thickness of the carrier element. Optionally, the thickness of the carrier element is in the range from 0.5 to 5 mm, optionally from 0.5 to 3 mm, optionally from 0.5 to 2 mm, optionally from 1 to 2 mm. Additionally or alternatively optional, the carrier element has an essentially flat top surface or an essentially flat bottom surface or both. Here, the term "plate-shaped carrier element" refers to an essentially flat element without any optional macroscopic protrusions on the top or bottom surface of the carrier element. Optionally, the top and bottom surfaces of the plate-shaped carrier element are essentially rectangular. Here, "essentially" means that the top or bottom surfaces may gave rounded corners and/or recesses at a rim area.

Receptacle Wall

The receptacle wall of a receptacle, optionally, includes all wall elements of the receptacle. Here, the receptacle wall may enclose the receptacle interior only partially in the sense that the wall body has the first and further openings. The wall body is the geometric body which is formed by the receptacle wall.

Edge

In this document, an edge is an essentially linear part of a surface along which sub-parts of the surface adjoin each other and are angled to one another. Applying this definition, each cubic has 12 edges, along each of which two sub-parts of the overall surface of the cubic adjoin each other and are angled to one another.

Primary Packaging Container

A primary packaging container is the packaging container that most closely protects the product in its distribution channels. The primary packaging container can also be referred to as retail or consumer packaging container. It follows that a test tube is not a primary packaging container.

The primary packaging containers may have any size or shape which the skilled person deems appropriate in the context of the invention. An optional primary packaging container is a primary packaging container for a medical, pharmaceutical or cosmetical composition. Optionally, the primary packaging container is suitable for packaging parenteralia in accordance with section 3.2.1 of the European Pharmacopoeia, $7^{th}$ edition from 2011. An optional primary packaging container is a vial, syringe, cartridge or ampoule.

Optionally, each of the primary packaging containers includes, in the following sequence along its length: a first end part, including a discharge orifice; a body part; and a further end part. Optionally, a first end part of the container includes a discharge orifice, which allows for discharging a medical, pharmaceutical or cosmetical composition from the container interior of the primary packaging container. In that case, the container wall of the primary packaging container encloses the container interior only partially. An optional primary packaging container, the first end part of which includes a discharge orifice is a vial, a syringe or a cartridge. An optional primary packaging container, the first end part of which does not include a discharge orifice, is an ampoule. In that case, the container wall of the primary packaging container entirely encloses the container interior. Additionally or alternatively optional, the further end part is a standing base, or includes a further orifice, or both. In the case of a further orifice, the primary packaging container, optionally, is a syringe. In the case of a standing base, the primary packaging container, optionally, is a vial, cartridge or ampoule. For an optional primary packaging container, the body part follows the first end part via a shoulder. This optional primary packaging container may be a vial, syringe, cartridge or ampoule, wherein a vial, cartridge or ampoule is optional. Additionally or alternatively optional, the further end part follows the body part via a heel. In that case, the primary packaging container, optionally, is a vial, cartridge or ampoule. Optionally, the body part is a lateral region of the primary packaging container. Optionally, the body part of the container wall forms a hollow cylinder. In case of a syringe, the body part of cylindrical shape is often referred to as barrel. Additionally or alternatively optional, the first end part includes, optionally consists of, from top to bottom of the primary packaging container a flange and a neck. In this case, the primary packaging container, optionally, is a vial, cartridge or ampoule.

The primary packaging container is optionally a glass container, a wall of glass (container wall) of which at least partially encloses a container interior of the primary packaging container. Optionally, the wall of glass is of a one-piece design. The wall of glass may optionally be made by blow molding a glass melt, or by preparing a tube of a glass, optionally in form of a hollow cylinder, forming the bottom of the container from one end of the tube, thereby closing the tube at this end, and forming the top region of the primary packaging container from the opposite end of the tube. Optionally, the wall of glass is transparent. Alternatively, the container wall is optionally made from a polymer. In that case, the container wall is also optionally to be transparent.

For the use in this document, the interior volume of the container interior represents the full volume of the interior of the primary packaging container. This volume may be determined by filling the interior of the primary packaging container with water up to the brim and measuring the volume of the amount of water which the interior can take up to the brim. Hence, the interior volume of the container interior as used herein is not a nominal volume as it is often referred to in the technical field of pharmacy. This nominal volume may for example be less than the interior volume by a factor of about 0.5.

Glass

The container wall of each of the primary packaging containers, optionally, includes a glass, more optionally essentially consists of the glass. This glass may be any type of glass and may have any composition which the skilled person deems suitable in the context of the invention. Optionally, the glass is suitable for pharmaceutical packaging. Optionally, the glass is of type I in accordance with the definitions of glass types in section 3.2.1 of the European Pharmacopoeia, 7$^{th}$ edition from 2011. Additionally or alternatively optional to the preceding, the glass is selected from the group consisting of a borosilicate glass, an aluminosilicate glass, and fused silica; or a combination of at least two thereof, wherein an aluminosilicate glass is optional. For the use in this document, an aluminosilicate glass is a glass which has a content of $Al_2O_3$ of more than 8 wt.-%, optionally more than 9 wt.-%, optionally in a range from 9 to 20 wt.-%, in each case based on the total weight of the glass. An optional aluminosilicate glass has a content of $B_2O_3$ of less than 8 wt.-%, optionally at maximum 7 wt.-%, optionally in a range from 0 to 7 wt.-%, in each case based on the total weight of the glass. For the use in this document, a borosilicate glass is a glass which has a content of $B_2O_3$ of at least 1 wt.-%, optionally at least 2 wt.-%, optionally at least 3 wt.-%, optionally at least 4 wt.-%, optionally at least 5 wt.-%, optionally in a range from 5 to 15 wt.-%, in each case based on the total weight of the glass. An optional borosilicate glass has a content of $Al_2O_3$ of less than 7.5 wt.-%, optionally less than 6.5 wt.-%, optionally in a range from 0 to 5.5 wt.-%, in each case based on the total weight of the glass. In a further aspect, the borosilicate glass has a content of $Al_2O_3$ in a range from 3 to 7.5 wt.-%, optionally in a range from 4 to 6 wt.-%, in each case based on the total weight of the glass.

A glass which is further optional according to the invention is essentially free from B. Therein, the wording "essentially free from B" refers to glasses which are free from B which has been added to the glass composition by purpose. This means that B may still be present as an impurity, but optionally at a proportion of not more than 0.1 wt.-%, optionally not more than 0.05 wt.-%, in each case based on the weight of the glass.

Medical, Pharmaceutical and Cosmetical Compositions

In the context of the invention, every medical composition, every pharmaceutical composition and every cosmetic composition, which the skilled person deems suitable, comes into consideration. A medical composition is a composition for the use in a medical treatment. A medical composition does not necessarily include an active ingredient. A pharmaceutical composition is a composition including at least one pharmaceutically active ingredient. An optional pharmaceutically active ingredient is a vaccine. A cosmetic composition is a composition including at least one cosmetically active ingredient. An optional cosmetically active ingredient is hyaluronic acid or botulinum toxin. The medical, pharmaceutical or cosmetical composition may be fluid or solid or both, wherein a fluid composition is particularly optional herein. An optional solid composition is granular such as a powder, a multitude of tablets or a multitude of capsules. A further optional medical, pharmaceutical or cosmetical composition is a parenterialium, i.e. a composition which is intended to be administered via the parenteral route, which may be any route which is not enteral. Parenteral administration can be performed by injection, e.g. using a needle (usually a hypo-dermic needle) and a syringe, or by the insertion of an indwelling catheter.

Secondary Packaging Container

The secondary packaging container may, generally, be any container which, for the skilled person, comes into consideration for accommodating the holding device, optionally the arrangement. An optional secondary packaging container is a tub. Optionally, the secondary packaging container is a tub of a so-called nested solution as they are generally known in the technical field of transport packaging for medical, pharmaceutical and cosmetical primary packaging containers. An example of a known nested solution is commercially available from Schott AG under the tradename SCHOTT iQ© platform. An optional secondary packaging container has been prepared by deep drawing or injection molding, where deep drawing is particularly optional. Additionally or alternatively optional, the secondary packaging container is made from one or more plastics. In this context, an optional plastic is one, selected from the group, consisting of: a polycondensation polymer, optionally polyethylene terephthalate; a polyacrylate, optionally polymethylmethacrylate; and a polyolefin, optionally polypropylene or polyethylene; or a combination of at least two thereof.

Directions

The lateral and longitudinal directions, as referred to herein, are perpendicular to one another. The longitudinal direction, optionally, extends along the lengths of the receptacles. Optionally, any direction, which is perpendicular to the longitudinal direction comes into consideration as lateral direction. Thus, a multitude of lateral directions may derive from a single longitudinal direction. Here, the lateral directions, optionally, form a plane which is perpendicular to the longitudinal direction. Optionally, this plane is a plane of plate-like extension of the plate-shaped carrier element. Any transversal section, herein, is perpendicular to the longitudinal direction.

Test Methods

The following test methods are to be used in the context of the invention. Unless otherwise specified, the measurements have to be carried out at an ambient temperature of 23° C., an ambient air pressure of 100 kPa (0.986 atm), and a relative atmospheric humidity of 50%.

Wall Thickness and Tolerance of Wall Thickness

The wall thickness and deviations from the mean value of the wall thickness (tolerance) are determined in accordance with the following standards for the respective type of container:

DIN ISO 8362-1 for vials;
DIN ISO 9187-1 for ampoules;
DIN ISO 110 4 0-4 for syringes;
DIN ISO 13926-1 for cylindrical cartridges; and
DIN ISO 11040-1 for dental cartridges.

Total Height $R_t$ of a Roughness Profile

The total height $R_t$ of a roughness profile is a profile roughness parameter. More specifically, the total height $R_t$ is the difference between the highest maximum and lowest minimum of the respective roughness profile.

The receptacle wall of each of the receptacles of the holding device according to the invention may consist of a single wall element or multiple wall elements. Further, the receptacle wall of each of the receptacles may be continuous or a have interruptions. Accordingly, the first and further edges may each be continuous or have interruptions. Further, the interior surface, the intermediate surface and also the lateral surface of the retaining part may have interruptions. Accordingly, any roughness profile, as used herein to determine a total height $R_t$ of the roughness profile, may be discontinuous, i.e., have one or multiple interruptions. In determining the total height $R_t$, those interruptions are ignored, in particular, not considered as a minimum of the roughness profile.

For determining the total height $R_t$ of a roughness profile, a digital microscope of the InfiniteFocusG5 plus type from Alicona Imaging GmbH and the software, that comes with it, are used. For the measurements, the objective lens with 4-times magnification is used. The Real3D-mode of the microscope allows creation of a 3D-dataset of the surface of interest. This 3D-dataset includes the roughness profile to be studied. Thus, the first and further ends of the receptacle as well as its interior surface are scanned using the Real3D-mode of the microscope. If the surface to be scanned is not accessible for the microscope, for example due to a small diameter of the receptacle, the nest is cut by hot-wire cutting. Here, the receptacle is cut into as few parts as necessary to render the surface of interest accessible for the 3D-scan. During cutting and handling of the nest, care has to be taken not to damage or modify the surface to be scanned. The 3D-datasets of multiple parts of a surface of interest are combined.

From the 3D-dataset of the respective surface of the receptacle, the total height $R_t$ of the roughness profile to be determined is derived. The roughness profiles of first and further edges can simply be extracted from the 3D-dataset of the surface which includes the respective edge. The $R_t$-value of such a roughness profile is the difference between its highest maximum and lowest minimum.

If not an edge but a surface—such as an intermediate surface, a lateral surface of a retaining part and an interior surface of a receptacle—is to be studied, the surface is fully covered with a grid of imaginary lines. The grid includes a first multitude of equidistant lines and a second multitude of equidistant lines. The lines of the first multitude are perpendicular to the lines of the second multitude. In case of a lateral surface of a retaining part and of an interior surface of a receptacle, each line of the first multitude is a, except for any potential interruptions, closed loop which is perpendicular to the longitudinal direction of the receptacle. In case, of an intermediate surface, the latter is fully covered with a rectangular grid of imaginary lines. In each case, the distance between neighbouring equidistant lines is 100 µm. For each of the equidistant lines of the first and second multitude, the total height $R_t$ of the roughness profile along this line is determined from the 3D-dataset. The $R_t$-value of the overall surface of interest is the maximum of the $R_t$-values of the lines of the first and second multitudes. This value is referred to as maximum total height $R_t$ of roughness profiles of the respective surface herein.

Transport Simulation

The transport simulation is conducted in accordance with ASTM D4169—16. In particular, the transport simulation consists of 2 sequences which are performed with the same sample one after the other. The environmental conditions in the test room are:

temperature: in the range from 15 to 35° C.
relative humidity: <85%
air pressure: in the range from 860 to 1060 hPa.

First Sequence

The first sequence is conducted in accordance with schedule A—Mechanical Handling—Unitized Loads as described in section 10.3.2 of ASTM D4169—16. A rotational flat drop test in accordance with ASTM D6179, method C is conducted. The drop height is selected from the table in section 10.3.2.3 of ASTM D4169—16 based on the assurance level II. The test includes 1 drop from each opposite base edge of the sample. One edge of the sample is supported by the floor. The other side is raised up to the drop height and released to fall flat on the impact surface (bottom of the wooden pallet). This procedure is performed with each opposite base edge which results in 4 drops altogether. The following test steps are performed:

1. Support edge 3-6 and raise edge 3-5; drop on face 3
2. Support edge 3-5 and raise edge 3-6 drop on face 3
3. Support edge 2-3 and raise edge 3-2; drop on face 3
4. Support edge 3-4 and raise edge 3-4; drop on face 3

If any of the boxes of the sample has moved on the pallet in one of the preceding steps 1. to 3., it is pushed back into place before the subsequent step. At the end of step 4, all boxes are pushed back to their original place on the pallet.

Second Sequence

The second sequence is conducted in accordance with schedule D—Stacked—Vibration as described in section 12.2 of ASTM D4169—16. A random vibration test in accordance with ASTM D4728 is conducted. In the test, the sample is in normal shipping orientation, i.e., with the wooden pallet at the bottom. The sample is loaded in accordance with section 11.4 of ASTM D4169—16. The top load TL is calculated from formula (3) as given in section 11.4 of ASTM D4169—16. Therein, H=2.7 µm and F=1. Further parameters of the second sequence are:

Truck Loop Profile:
0.40 G., for 40 min
0.54 Grms for 15 min
0.70 Grms for 5 min
Numbers of Loops: 1
Duration in Total: 1 h on Face 3;
Air Profile:
AL II/Grms: 1.05
Test Duration: 2 h on Face 3.

Particle Load after Transport Simulation

Directly after the sample has been subjected to the above transport simulation, the particle load of the exterior surfaces of the primary packaging containers (syringes) as have been held in the holding device to be studied is determined in particles of a specific size range (particle class) per $cm^2$ of the sum of the surface areas of the exterior surfaces. Any further handling of the sample which could lead to the formation of further particles is to be avoided between the transport simulation and determination of the particle load.

Liquid Particle Counting System

The particle load of the primary packaging containers of the holding device to be studied is determined using a liquid particle counting system which includes a particle counter Pacific Scientific Hiac Royco, Model 9703 (F4-088) and a desktop computer on which runs the software PharmSpec 3.4.0 as it comes with the particle counter. Generally, the particle counter draws up the test liquid via an ascending pipe and guides it past a scattered light sensor. The signals coming from the scattered light sensor are read out and processed by the software. In this test method, only particle-free water which has been prepared by an H2O-EDI-2-T arium® advance EDI (10 l/h) tabletop system from Sartorius AG, Göttingen, Germany is used for cleaning, for flushing and rinsing, as zero sample, for any filter exchange and for preparing the test liquid. This system is an apparatus for preparing pure water of type 2. The system has a flow performance of 10 liters per hour.

Preparation of the Particle Counter

The medium required for flushing (particle-free water) and testing (test liquid) is filled into the vessel at least 1 hour before the test. The particle counter is operated under laminar flow conditions. Prior to the start of the tests, the complete laminar flow workstation running with working flow is cleaned with a moistened particle-free cloth. The lifting arm to which the suction pipe is attached can be controlled via the control panel. Before the first measurement can be carried out, the sampler must be cleaned and adjusted so that the suction tube is immersed as deeply as possible in the test liquid without touching the bottom of the vessel. The adjustment is carried out with the vessel with which the later measurements are also carried out. The lowest position of the lifting arm is saved and then the lifting arm is moved back to the starting position. In order to clean the sampler, a vessel which has been flushed 3 times with particle-free water is filled with at least 35 ml of particle-free water and positioned under the lifting arm. The lifting arm is moved into the lower position which has been saved as described above. Again, the lifting arm must not touch the bottom of the vessel. The automatic flushing sequence is started. Per cleaning run 10 ml of liquid consumed. Four cleaning runs are conducted. Under no circumstances should air be sucked in. Therefore, there must be at least 35 ml of particle-free water in the vessel. After cleaning, the lifting arm is moved to the upper position.

Zero Sample

Before starting the tests, the particle-free water used to prepare the test liquid must be checked for its particle content. For this purpose, the vessel which will be used for the measurements is rinsed 3 times with particle-free water. Then, the vessel is filled with 40 ml of the particle-free water as zero sample. After the zero sample has been left to stand for at least 2 minutes to deaerate, the test can be started. The particle counter measures the number of particles in a given volume of the particle-free water. Here, particles of all particle sizes possible have to be recorded. For this, the machine draws up and tests 6 times 5 ml of liquid. The first measurement is rejected. An acceptance criterion is set to a maximum of 25 particles of particle size of at least 10 µm per 25 ml of the particle-free water. If this value is not met, preparation of the particle-free water must be adapted and measurement of the zero sample must be repeated until the acceptance criterion is met.

Test Liquid

The stretch foil is removed from the cardboard boxes. The box which contains the holding device to be studied is taken from the pallet and opened under laminar flow. All further steps are conducted under laminar flow. The arrangement of holding device and primary packaging containers to be studied is taken out of the box. A glass beaker with enough particle-free water for immersing one of the primary packaging containers (syringes) from the holding device at a time to half of its length in the water in an upright orientation is prepared. In any case, a minimum of 40 ml of particle-free water is used and referred to as pool in the following. The glass beaker is flushed at least 3 times with particle-free water beforehand. All openings of the primary packaging containers from the holding device to be studied are closed by stoppers which have been rinsed at least 3 times with particle-free water beforehand. This should ensure that only particles from the exterior surfaces of the primary packaging containers will be collected in the test liquid. One after the other, each of the primary packaging containers is immersed to half of its length in the pool (the same particle-free water) in an upright orientation and manually agitated to make a stirring motion while maintaining the upright orientation for 5 s. As syringes are used as primary packaging containers in the example and the comparative example described below, the upright orientation means that the tips of the syringes face upwards. The test liquid is the pool in which all the primary packaging containers from the holding device to be studied have been washed as described in the preceding.

Measurement

The test liquid is filled into the vessel at least 1 hour before the test. The particle counter measures the number of particles of particle sizes of $\geq 2$ µm, $\geq 5$ µm, $\geq 10$ µm, $\geq 15$ µm, $\geq 25$ µm, $\geq 50$ µm, $\geq 75$ µm and $\geq 100$ µm. For this, the machine tests 6 times 5 ml of the test liquid and rejects the first measurement. Therefore, the minimum volume of the test liquid is 35 ml. For each of the above particle size classes, the number of particles per $cm^2$ is determined by dividing the number particles in the test liquid as determined by the particle counter by the sum of the area of the exterior surfaces of the primary packaging containers from the holding device to be studied.

The invention is set out in more detail below by way of examples and figures, with the examples and figures not denoting any restriction on the invention. Furthermore, unless otherwise indicated, the figures are not to scale.

Preparation of Holding Devices

Holding devices, also referred to as nests, of the design as shown in FIGS. 1 and 2 are prepared from polypropylene by injection molding. The terms used below to refer to specific sites of these holding devices, such as first and further edges, intermediate surfaces and interior surfaces of receptacles, are explained in the descriptions of FIGS. 1 and 2. Those terms are used in line with the terminology as used in this document to describe the invention.

The holding devices of the comparative example are not post-treated after demolding and before being loaded with syringes as primary packaging containers, in particular not deburred. Optical Microscope studies show that these holding devices have burrs on various sites of their surface, in particular on the first and further edges of the receptacles, on the intermediate surfaces between first and further edges and on the interior surfaces of the receptacles. The height of these burrs is often in the range from 90 to 150 µm. The height of a considerable amount of the burrs is significantly greater, such as more than 500 µm. One exemplary burr is shown in the microscope image of FIG. 15. The total height $R_t$ of a roughness profile can be expected to be at least as high as the highest burr which lies on that roughness profile.

For each of the examples 1 to 4, a deburring procedure is applied to specific sites of the holding devices after demolding and before loading with syringes. These sites are selected from those which would show burrs without deburring, i.e., the first and further edges of the receptacles, the intermediate surfaces between first and further edges and the interior surfaces of the receptacles. Table 1 below summarizes which sites are deburred in which of the examples. In each case, the deburring is effected manually by carefully and thoroughly treating the respective site with a deburring knife. For deburring edges, a deburring knife of the type GRATTEC Keramicut ROTO 75° from IBT Ingenieurburo Thiermann GmbH, Wiesbaden in Germany is used. For deburring surfaces, a deburring knife of the type GRATTEC Keramicut I, also from IBT Ingenieurburo Thiermann GmbH, Wiesbaden in Germany, is used. Optical Microscope studies show that burrs as the one in FIG. 15 can be avoided by applying this procedure.

TABLE 1

| | First Edge | Further Edge | Intermediate Surface | Interior Surface |
|---|---|---|---|---|
| Comparative Example | Not Deburred | Not Deburred | Not Deburred | Not Deburred |
| Example 1 | Deburred | Not Deburred | Not Deburred | Not Deburred |
| Example 2 | Deburred | Deburred | Not Deburred | Not Deburred |
| Example 3 | Deburred | Deburred | Deburred | Not Deburred |
| Example 4 | Deburred | Deburred | Deburred | Deburred |

After the holding devices of the comparative example and the examples 1 to 4 have been prepared as described above, the total heights $R_t$ of roughness profiles of first and further edges of receptacles and the maximum total heights $R_t$ of roughness profiles of intermediate surfaces between first and further edges and of the interior surfaces are determined according to the test method as described above. Those total heights $R_t$ of roughness profiles (also referred to as $R_t$-values) are determined for each of the receptacles of 10 arbitrarily selected holding devices per comparative example and example.

The results show that for less than 50% of the receptacles of the holding devices of the comparative example, the preceding $R_t$-values are 500 μm or less. For significantly more than half of those receptacles, the preceding $R_t$-values are larger than 90 μm. For practically none of the receptacles of the 10 holding devices of the comparative example the preceding $R_t$-values are 20 μm or less. The non-deburred sites of the holding devices of the examples 1 to 3 show similar $R_t$-values as corresponding sites of the holding devices of the comparative example. In contrast, in the examples 1 to 4, practically all of the $R_t$-values of deburred sites are 500 μm or less. Still close to 100% of the $R_t$-values of deburred sites are 90 μm or less and at least 50% of the $R_t$-values of deburred sites are 20 μm or less.

Transport Simulation

Each of the holding devices of each of the comparative example and the examples 1 to 4 is fully loaded with 64 empty syringes with their stoppers, but without plungers. The syringes are of the TopPac® 5 ml lg type as is commercially available from Schott AG. Such a syringe is schematically shown in FIG. 5. The container walls of the syringes consist of a cyclic olefin copolymer (COC). The syringes are held in the receptacles of the holding devices as schematically shown in FIG. 10.

Each of the loaded nests (holding devices) of the comparative example and the examples 1 to 4 is placed into a tub. Generally, a tub with a loaded nest can be seen in FIG. 3. In the figure, the nest design is slightly different. Accordingly, the number and arrangement of receptacles and, thus, syringes are different from the actual nests of the comparative example and the examples. FIG. 3 is referred to for illustrative purposes in regard of the general nature of a loaded nest in a tub only. Each filled tub is closed by sealing a gas-permeable lid onto the upper rim of the tub via a hotmelt. In FIG. 3, the lid has been peeled off partially.

For each of the comparative example and the examples 1 to 4, a sample is prepared for a transport simulation. Each sample is a pallet unit which includes a wooden pallet on which boxes of corrugated cardboard are stacked such that the overall dimensions of the sample are length: 1200 mm, width: 800 mm and height: 940 mm.

The boxes are tightly secured to each other by plastic stretch foil. For each of the comparative example and the examples, the boxes are filled with identical tubs which have been filled with loaded nests and sealed as described. The boxes do not contain any additional filling material.

For each of the comparative example and the examples, the transport simulation is conducted as described above in the test methods section. After the transport simulation, particle loads on the exterior surfaces of the syringes are determined as further described in the above test methods section.

Evaluation

FIG. 16A shows a photograph of a typical syringe of the comparative example after the corresponding sample has been subjected to the transport simulation. Clearly, many macroscopic particles can be seen on the exterior surface. The majority of these particles stems from the nest and, thus, consists of polypropylene. FIG. 16B is a photograph of a typical syringe of the example 4 after the corresponding sample has been subjected to the transport simulation. In contrast to FIG. 16A, only very few particles can be seen on the exterior surface of the syringe in FIG. 16B.

These results are surprising because the deburring post-treatment and the handling of the nests involved have been expected to cause significant generation of polypropylene particles. This is in particular because deburring means to cut parts from the holding devices. The cutting has been expected to produce a significant amount of macroscopic and microscopic particles. In contrast to this technically very plausible expectation, the results of the studies reveal that the particle generation caused by rather high $R_t$-values during the transport simulation widely outweighs the particle generation effect of the deburring procedure.

The qualitative results as described above by reference to FIGS. 16A and 16B are supported by the quantitative measurements of the particle loads on the exterior surfaces of the syringes after the transport simulation. Table 2 below summarizes the results of the particle load measurements by providing a comparison of the loads of particles of 2 different size classes for the syringes of the comparative example and the examples 1 to 4. In the Table 2, +++ means less particles than ++, which means less particles than +, which means less particles than 0, which means less particles than −, which means still less particles than −−.

TABLE 2

|  | Number of Particles of Particle Size ≥ 5 μm per cm² | Number of Particles of Particle Size ≥ 2 μm per cm² |
|---|---|---|
| Comparative Example | − | −− |
| Example 1 | + | 0 |
| Example 2 | ++ | + |
| Example 3 | +++ | ++ |
| Example 4 | +++ | +++ |

The results of the studies clearly show that the loads of particles with particle sizes of at least 5 μm, but also the loads of particles with particle sizes as small as 2 μm are reduced by $R_t$-values which are at 500 μm or below, and which still close to all are at 90 μm or below, and at least 50% of which are 20 μm or less.

In the field of pharmaceutical packaging, contamination of syringes with any kind of mobile particles has to be avoided strictly, in particular if parenteralia are packaged. Specifically, particles as small as 2 to less than 5 μm post a severe safety issue on syringes as those particles can get into the syringe interior on the filling line and, in the worst case, could be injected into a patient. In addition, larger particles on the syringe surfaces may hamper optical inspection of the syringes for quality control. It follows from the test results as presented above, that the invention allows improvement of safety in pharmaceutical packaging and further allows improvement of quality control of pharmaceutical primary packaging containers.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 9A shows a further scheme of the section through the receptacle in FIG. 8;

FIG. 9B shows a scheme of a transversal section in the transversal plane in FIG. 9A;

FIG. 10 shows a scheme of a section through a further receptacle of a holding device according to the invention;

FIG. 11 shows a scheme of a section through a further receptacle of a holding device according to the invention;

FIG. 14A shows a scheme of a section through part of a receptacle of a holding device according to the invention;

FIG. 14B shows a scheme of a section through part of a further receptacle of a holding device according to the invention;

Corresponding reference characters indicate corresponding parts throughout the several views. The exemplification set out herein illustrate embodiments of the invention, and such exemplifications are not to be construed as limiting the scope of the invention in any manner.

DETAILED DESCRIPTION OF THE INVENTION

Figure 1:
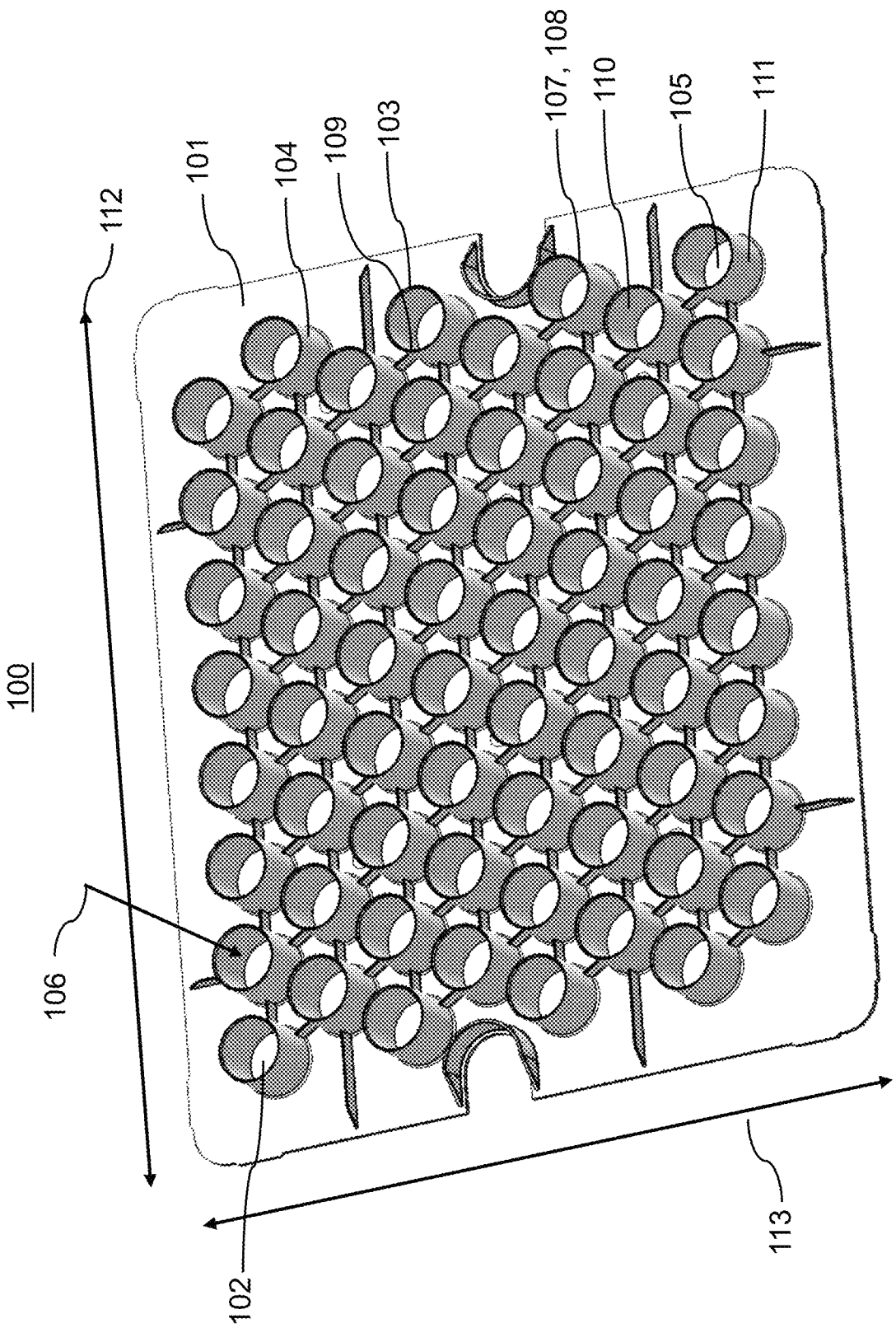
FIG. 1 shows a scheme of a holding device according to the present invention from above.

FIG. 1 shows a scheme of a holding device 100, according to the invention, for holding a plurality of primary packaging containers 304 for pharmaceutical, medical or cosmetic compositions. The holding device 100 is shown from above. It has been prepared from polypropylene by injection molding. The holding device 100 includes a plate-shaped carrier element 101 which includes a plurality of through-holes 102. The term "plate-shaped" refers to a width 113 and a length 112 of the plate-shaped carrier element 101 being more than 50 times a thickness of the carrier element. Here, the thickness is 1 mm. Further, the holding device 100 includes a plurality of receptacles 103, each of which is designed and arranged to accommodate one of the primary packaging containers 304. Each of the receptacles 103 includes a receptacle wall 104 which partially encloses a receptacle interior 105. Each receptacle wall 104 forms a wall body which extends in a longitudinal direction 106 through one of the through-holes 102 of the plurality of through-holes 102. Here, the wall bodies are hollow cylinders. For each of the receptacles 103, the wall body has an interior surface 110, which faces the receptacle interior 105, and an exterior surface 111 which faces opposite to the interior surface 110. Further, each wall body has a first opening 107 at a first end 108. The first opening 107 of each wall body is laterally directly surrounded by a first edge 109 of the respective wall body. Each of the receptacles 103 has a total height $R_t$ of a roughness profile of its first edge 109 of not more than 0.5 mm.

Figure 2:
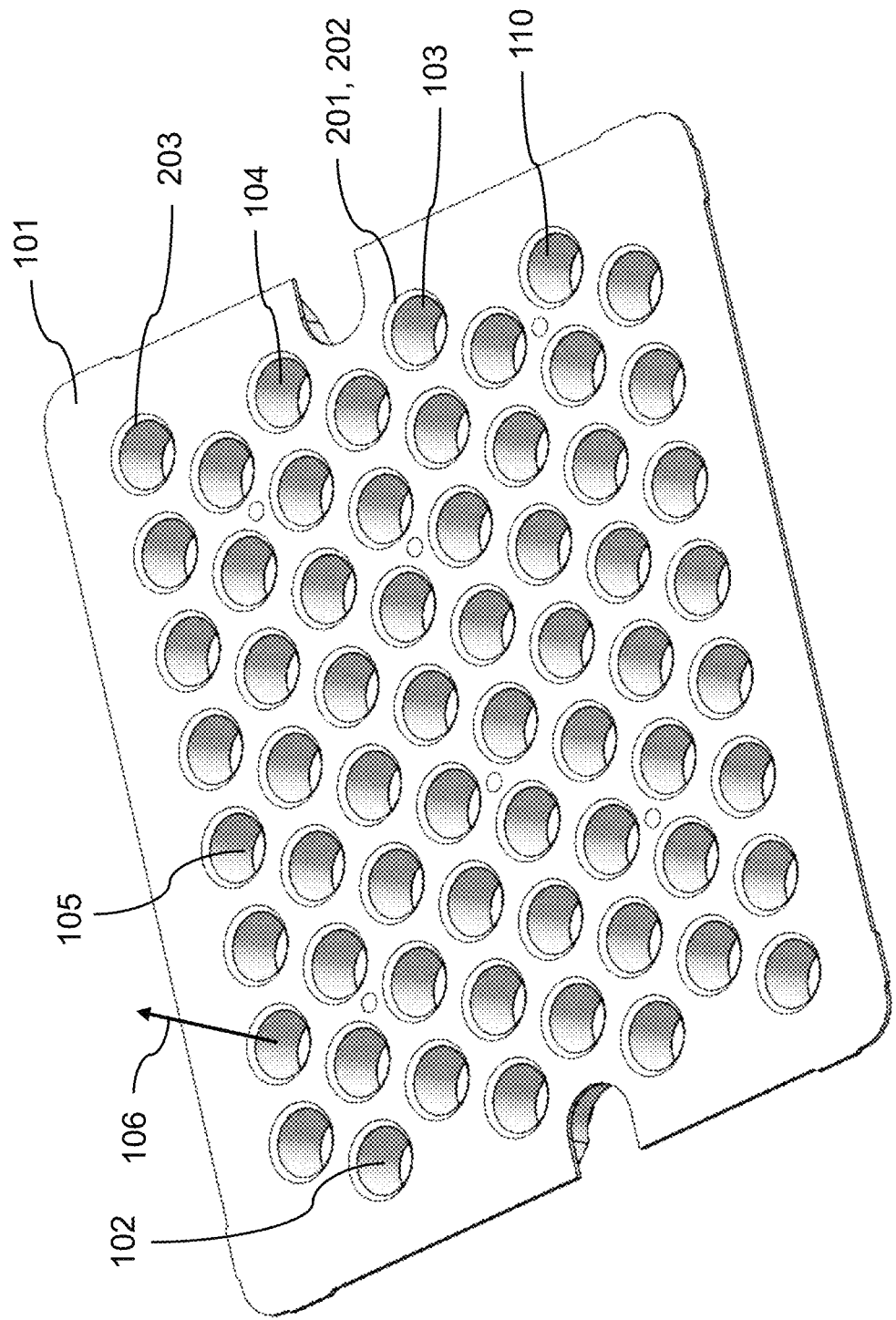
FIG. 2 shows a scheme of the holding device in FIG. 1 from below.

FIG. 2 shows a scheme of the holding device 100 in FIG. 1 from below. In this view, it can be seen that each wall body, additionally, has a further opening 201 at a further end 202 which, in the longitudinal direction 106, is opposite to the first end 108 (see FIG. 1). Each further opening 201 is laterally directly surrounded by at least one further edge 203 of the respective wall body. Each of the receptacles 103 has a total height $R_t$ of a roughness profile of its further edge 203 of not more than 0.5 mm.

Figure 3:
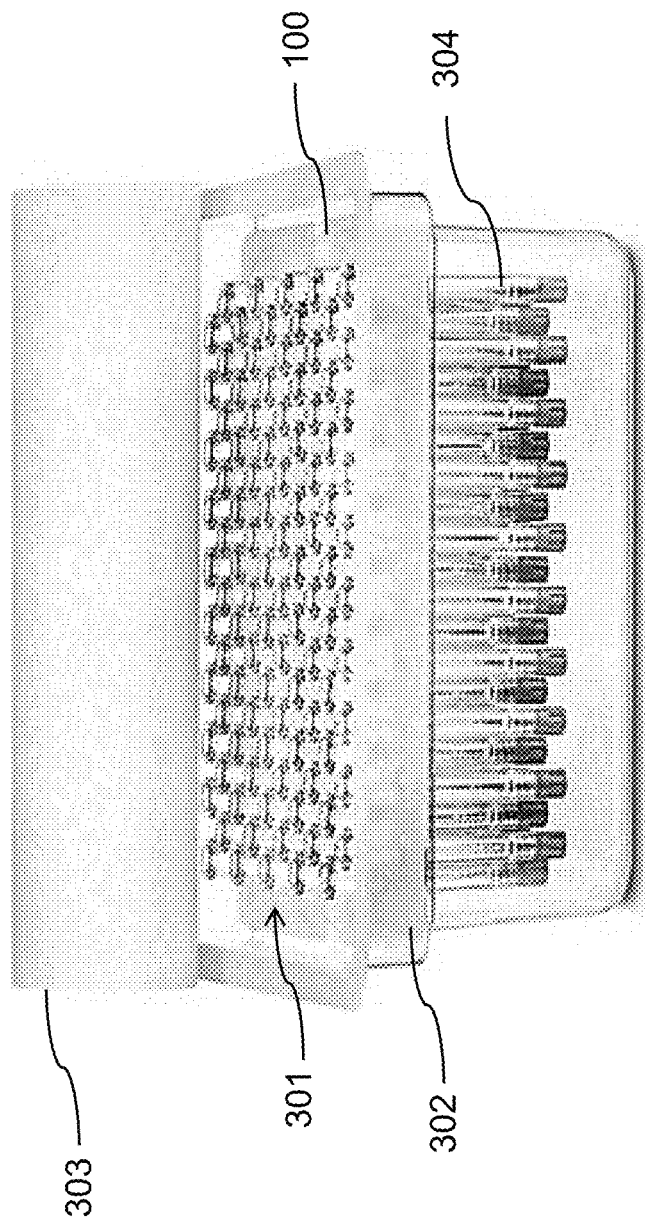
FIG. 3 shows a scheme of a transport unit according to the invention.

FIG. 3 shows a scheme of a transport unit 300 according to the invention. The transport unit 300 includes an arrangement 301 according to the invention and a secondary packaging container 302. The latter is a tub which has been prepared from plastics by deep-drawing. The tub was closed with a gas-permeable lid 303 which was joined to the tub but has partially been peeled off to reveal the arrangement 301 inside the tub. The arrangement 301 includes a holding device 100 according to the invention and a plurality of primary packaging containers 304, each of which is accommodated in one of the receptacles 103 of the holding device 100.

Figure 4:
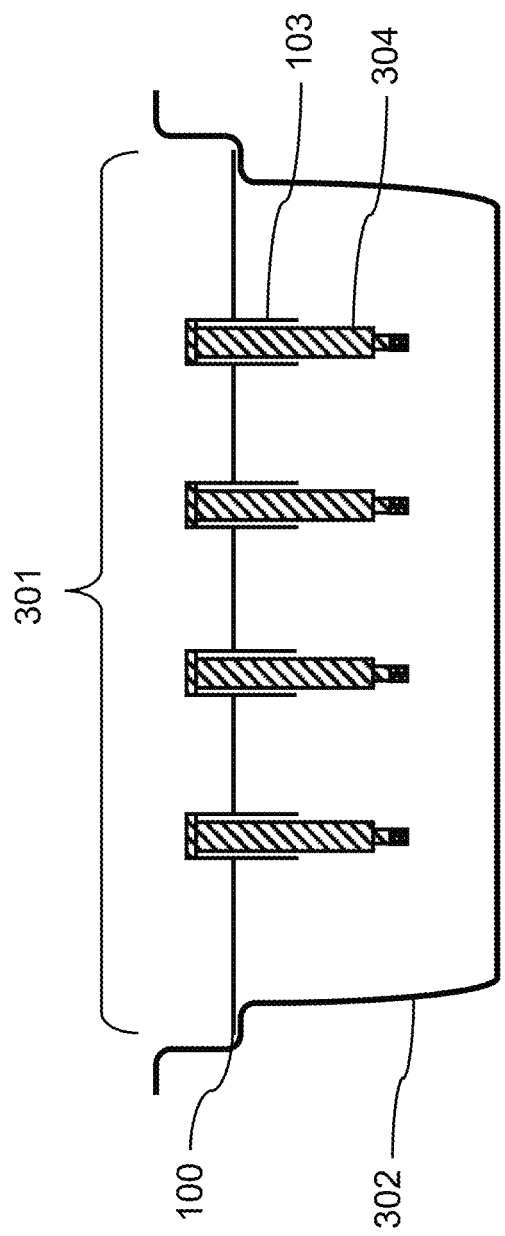
FIG. 4 shows a section through a transport unit according to the invention.

FIG. 4 shows a section through a transport unit 300 according to the invention. This transport unit 300 also includes an arrangement 301 according to the invention and a secondary packaging container 302 which is a tub. The latter has been prepared from plastics by deep-drawing. The arrangement 301 includes a holding device 100 according to the invention and a plurality of primary packaging containers 304, each of which is accommodated in one of the receptacles 103 of the holding device 100. Here, the primary packaging containers 304 are syringes. The holding device 100 has been prepared from plastics by injection molding.

Figure 5:
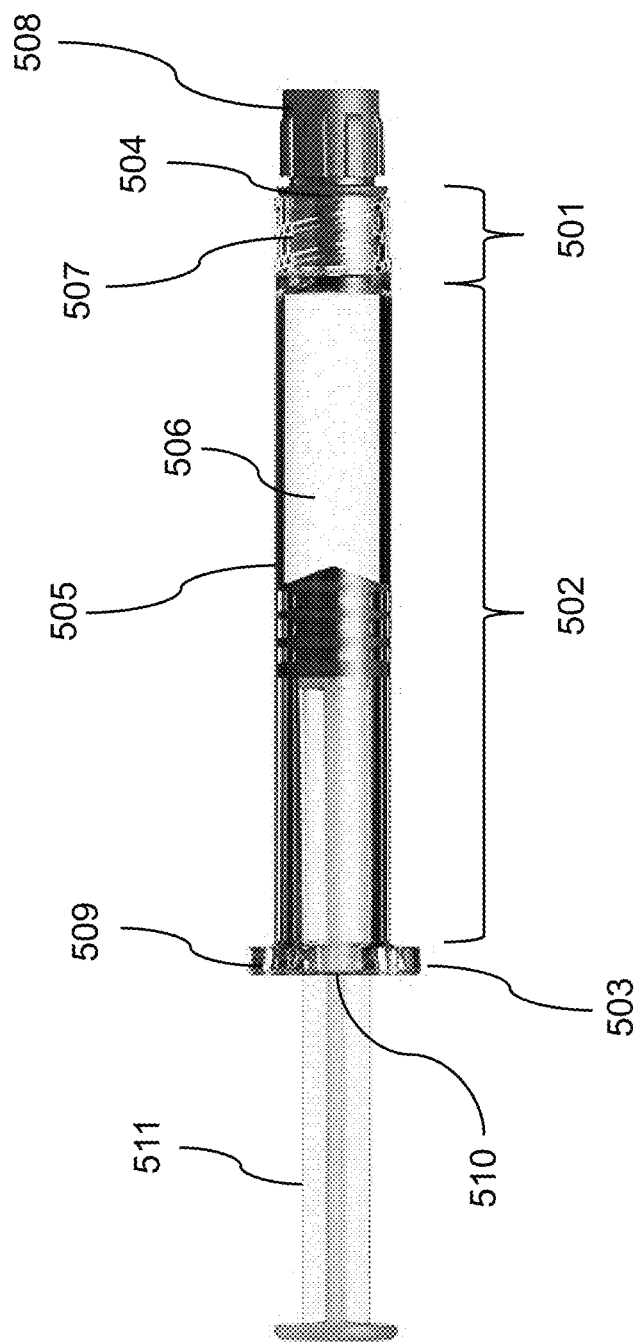
FIG. 5 shows a scheme of a primary packaging container.

FIG. 5 shows a scheme of a primary packaging container 304 which is a TopPac© 5 ml lg type syringe from Schott AG. The syringe 101 includes a container wall 505 which partially surrounds a container interior 506. The container wall 505 is made from a cyclic olefin copolymer (COC) and forms, in the following sequence from top to bottom (based on the syringe itself and from right to left in the figure), a first end part 501, including a discharge orifice 504; a body part 502; and a further end part 503. The body part 502, which in the art is also referred to as barrel, is a hollow cylinder. The further end part 503 includes a further orifice 510. The discharge orifice 504 has an orifice area which is less than an orifice area of the further orifice 510. The further orifice 510 accommodates a plunger 511. The further end part 503 further includes a rim 509, in the art also referred to as a flange, which projects laterally from beyond the body part 502 and hems the further orifice 510. The container wall 505 is made from a cyclic olefin copolymer. The first end part 501 includes a connecting element which is a male part 507 of a Luer taper. The connecting element includes a thread for connecting a hypodermic needle to the syringe. The thread is arranged in a sleeve. The syringes of the arrangements 301 in FIGS. 4, 8 and 10 to 13 are syringes of the type shown in FIG. 5, however, without the plunger 511.

Figure 6:
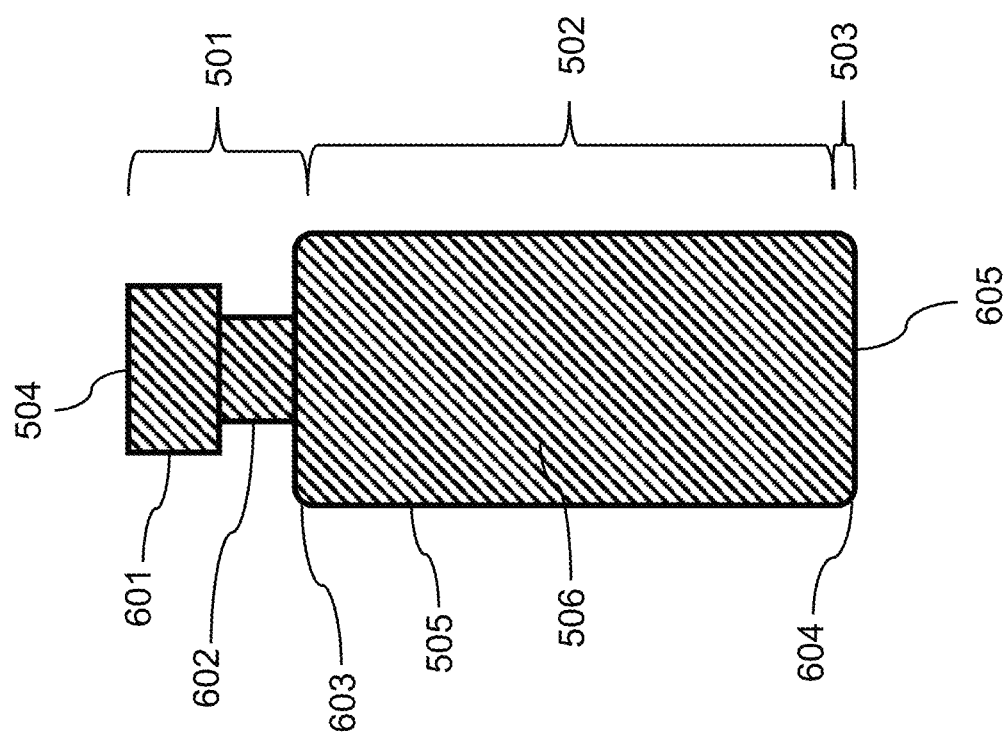
FIG. 6 shows a scheme of a further primary packaging container.

FIG. 6 shows a scheme of a further primary packaging container 304 which is a vial. The latter includes a container wall 505 which partially surrounds a container interior 506. The container wall 505 forms, in the following sequence from top to bottom, a first end part 501, including a discharge orifice 504; a body part 502; and a further end part 503. The body part 502 is a hollow cylinder. The further end part 503 includes a standing base 605. Besides the discharge orifice 504, the first end part 501 includes a flange 601 and a neck 602. The body part 502 follows the first end part 501 via a shoulder 603. The further end part 503 follows the body part 502 via a heel 604. The container wall 505 is made from type I borosilicate glass.

Figure 7:
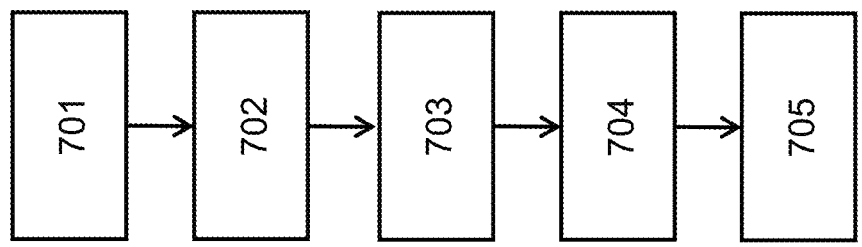
FIG. 7 shows a flow-chart of a process of producing a holding device according to the invention.

FIG. 7 shows a flow-chart of a process 700 of producing a holding device 100 according to the invention by injection molding. The process 700 includes process steps of: a) 701 providing a first part of a mold and a further part of the mold; b) 702 positioning the first part and the further part relative to one another such that the first part and the further part together at least partially enclose an interior of the mold; c) 703 introducing a polymer melt into the interior of the mold; d) 704 solidifying the polymer melt in the interior of the mold, thereby obtaining a molded body; and e) 705 demolding the molded body.

Figure 8:
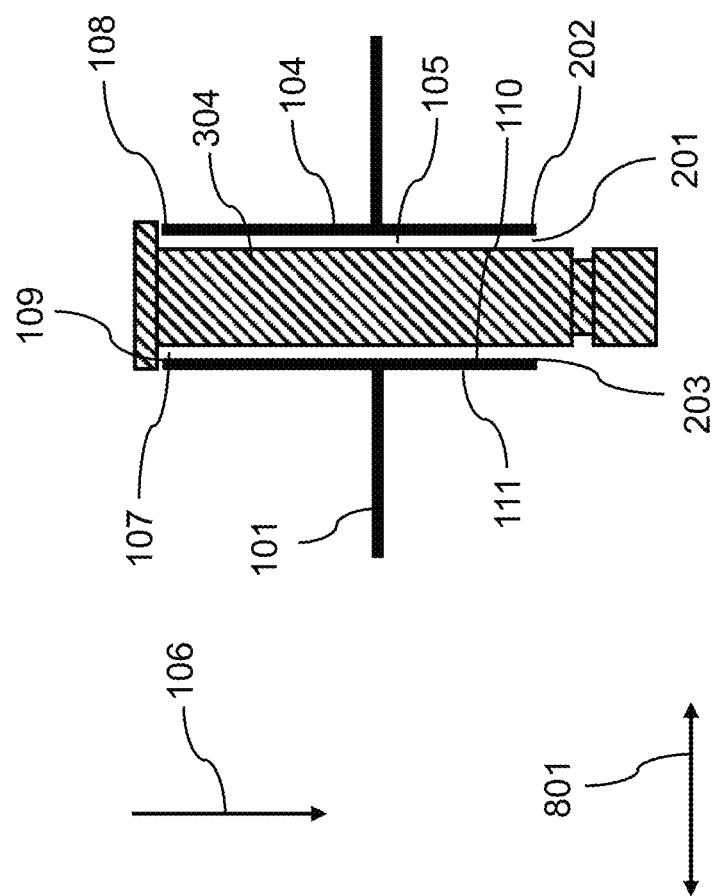
FIG. 8 shows a scheme of a section through a receptacle of the holding device of FIG. 4.

FIG. 8 shows a scheme of a section through a receptacle 103 of the holding device 100 of FIG. 4. Here, only part of the holding device 100 is shown. Accordingly, only part of the plate-shaped carrier element 101 is shown. A primary packaging container 304, which is a syringe of the type as shown in FIG. 5, is accommodated in the receptacle 103. The receptacle 103 includes a receptacle wall 104 which partially encloses a receptacle interior 105. The receptacle wall 104 forms a wall body which extends in a longitudinal direction 106. The lateral directions 801 are perpendicular to the longitudinal direction 106.

The wall body has an interior surface 110, which faces the receptacle interior 105, and an exterior surface 111 which faces opposite to the interior surface 110. Further, the wall body has a first opening 107 at a first end 108. The first opening 107 is laterally directly surrounded by exactly one first edge 109 of the wall body. Here, the first edge 109 is the inner edge of receptacle wall 104 at the first end 108. A total height $R_t$ of a roughness profile of the first edge 109 is not more than 0.05 mm. This holds for at least 90% of the receptacles 103 of the holding device 100 of the arrangement 301 in FIG. 4. Furthermore, the wall body has a further opening 201 at a further end 202 which, in the longitudinal direction 106, is opposite to the first end 108. The further opening 201 is laterally directly surrounded by exactly one further edge 203 of the wall body. Here, the further edge 203 is the inner edge of receptacle wall 104 at the further end 202. A total height $R_t$ of a roughness profile of the further edge 203 is also not more than 0.05 mm. This also holds for at least 90% of the receptacles 103 of the holding device 100 of the arrangement 301 in FIG. 4.

FIG. 9A shows a further scheme of the receptacle 103 in FIG. 8. This scheme lacks the syringe from FIG. 8. The wall body of the receptacle 103 has 2 intermediate surfaces 901 which are neither part of the interior surface 110 nor of the exterior surface 111. One of intermediate surfaces 901 faces in the longitudinal direction 106 and the other in the counter direction of the longitudinal direction 106. The intermediate surface 901 at the first end 108 is located between the first edge 109 and the outer edge of receptacle wall 104 at the first end 108. The intermediate surface 901 at the further end 202 is located between the further edge 203 and the outer edge of receptacle wall 104 at the further end 202. For each of the 2 intermediate surfaces 901, the roughness profiles have a maximum total height $R_t$ of not more than 0.050 mm. This is true for at least 90% of the receptacles 103 of the holding device 100 of the arrangement 301 in FIG. 4. A dashed line in FIG. 9A depicts a plane 902 of the transversal section 904 through the receptacle 103 which is shown in FIG. 9B. This transversal section 904 is exemplary of all the transversal sections 904 through the receptacle 103 which includes a part of the interior surface 110. The wall body is axially symmetric around a central longitudinal axis 903. Accordingly, the first 107 and further openings 201 are circular, and the first 109 and further edges 203 are circle lines (see also FIG. 9B).

FIG. 9B shows a scheme of an exemplary transversal section 904 through the receptacle 103 in FIG. 9A. The maximum total height $R_t$ of roughness profiles of the interior surface 110 is not more than 0.070 mm. This holds for at least 80% of the receptacles 103 of the holding device 100 of the arrangement 301 in FIG. 4.

FIG. 10 shows a scheme of a further receptacle 103 of a holding device 100 according to the invention. Just as in FIG. 8, only part of the holding device 100 and only part of the plate-shaped carrier element 101 is shown. A primary packaging container 304, which is a syringe of the type as shown in FIG. 5, is accommodated in the receptacle 103. The receptacle 103 in FIG. 10 is designed as the one in FIG. 8, however, in FIG. 10 the receptacle wall 104 has a further edge 203, but no outer edge at the further end 202. This is because the further end 202 is flush with the plate-shaped carrier element 101.

FIG. 11 shows a scheme of a further receptacle 103 of a holding device 100 according to the invention. Just as in FIG. 8, only part of the holding device 100 and only part of the plate-shaped carrier element 101 is shown. A primary packaging container 304, which is a syringe of the type as shown in FIG. 5, is accommodated in the receptacle 103. The receptacle 103 in FIG. 11 is designed as the one in FIG. 8, however, in FIG. 11 the wall body includes a retaining part 1101. The latter extends laterally, i.e., in the lateral directions 801, and limits the receptacle interior 105 in the longitudinal direction 106. Further, the retaining part 1101 includes the further opening 201. In consequence, the receptacle has 2 further edges 203. Those are the upper and lower edges of a lateral surface 1102 of the retaining part 1101. The lateral surface 1102 directly surrounds the further opening 201. The maximum total height $R_t$ of roughness profiles of the lateral surface 1102 is not more than 0.050 mm.

Figure 12:
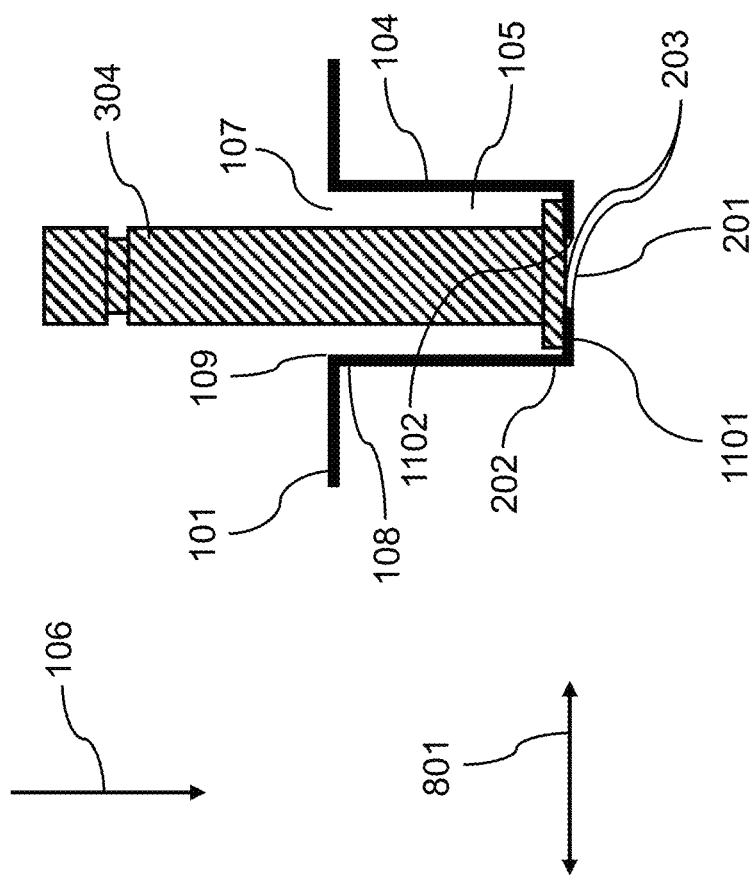
FIG. 12 shows a scheme of a section through a further receptacle of a holding device according to the invention.

FIG. 12 shows a scheme of a further receptacle 103 of a holding device 100 according to the invention. Just as in FIG. 11, only part of the holding device 100 and only part of the plate-shaped carrier element 101 is shown. A primary packaging container 304, which is a syringe of the type as shown in FIG. 5, is accommodated in the receptacle 103. The receptacle 103 in FIG. 12 is designed as the one in FIG. 11, however, in FIG. 12 the receptacle wall 104 has a first edge 109, but no outer edge at the first end 108. This is because the first end 108 is flush with the plate-shaped carrier element 101.

Figure 13:
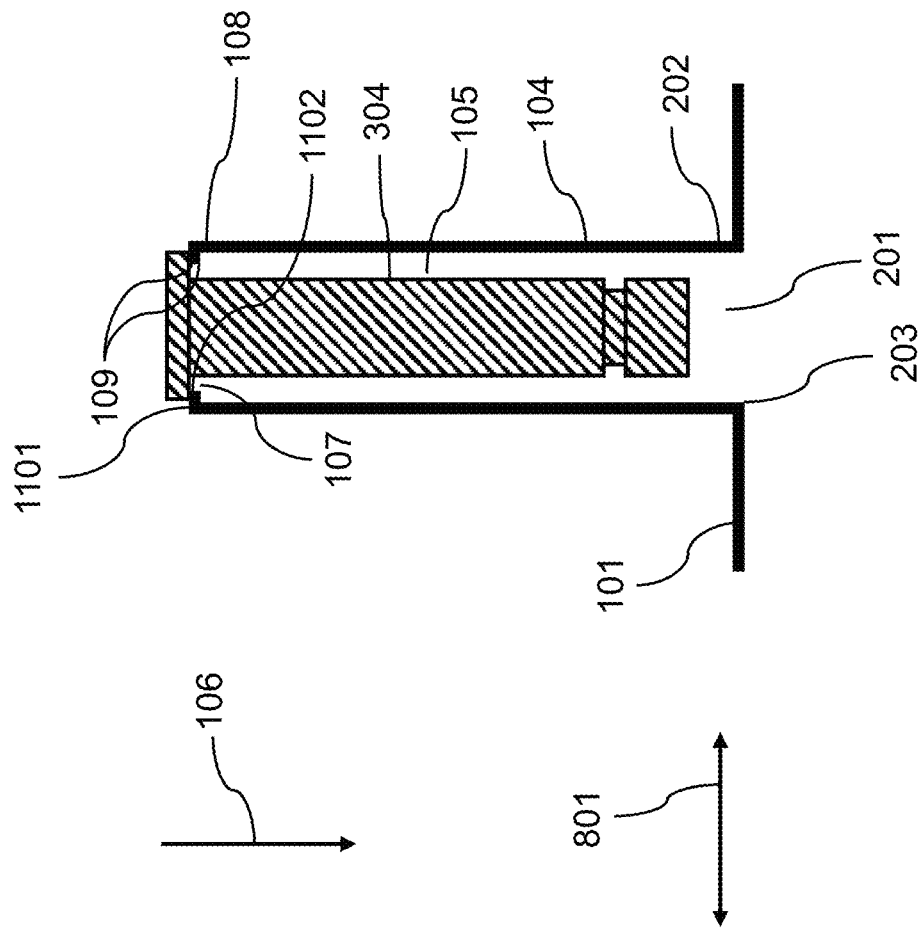
FIG. 13 shows a scheme of a section through a further receptacle of a holding device according to the invention.

FIG. 13 shows a scheme of a further receptacle 103 of a holding device 100 according to the invention. Just as in FIG. 12, only part of the holding device 100 and only part of the plate-shaped carrier element 101 is shown. A primary packaging container 304, which is a syringe of the type as shown in FIG. 5, is accommodated in the receptacle 103. The general design of the receptacle 103 in FIG. 13 is the same as in FIG. 11, however, upside-down.

FIG. 14A shows a scheme of a section through part of a receptacle 103 of a holding device 100 according to the invention. More specifically, FIG. 14A shows the first end 108 of the wall body of the receptacle in FIG. 8. Here, the syringe is not shown. This figure is meant to provide a closer view on the position of the first edge 109 and the intermediate surface 901.

FIG. 14B shows a scheme of a section through part of a receptacle 103 of a holding device 100 according to the invention. More specifically, FIG. 14B shows the first end 108 of the wall body of the receptacle in FIG. 2. Here, the syringe is not shown. This figure is meant to provide a closer view on the position of the first edge 109 and the intermediate surface 901.

Figure 15:
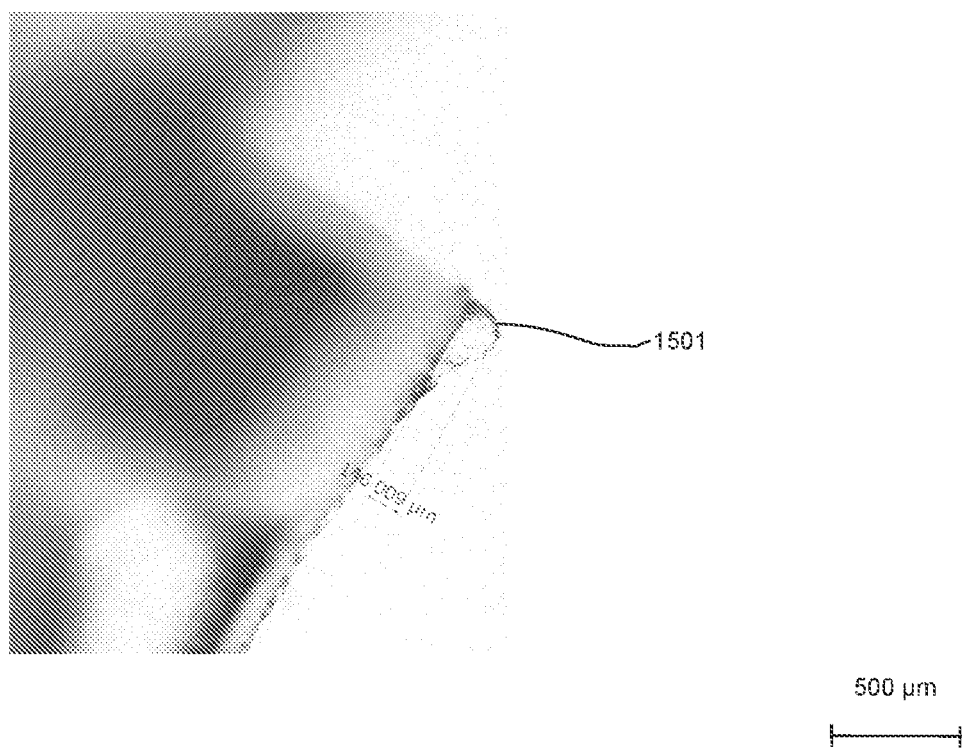
FIG. 15 shows an optical microscope image of a burr on an edge of a receptacle.

FIG. 15 shows an optical microscope image 1500 of a burr 1501 on an edge of a receptacle. The height of the burr 1501 is 146.009 µm. This burr 1501 is the highest site on this edge. Further, the height of the burr 1501 is much more than any valley on the roughness profile of the edge. Accordingly, the total height $R_t$ of the roughness profile of the edge with the burr 1501 is only slightly above 146 µm.

Figure 16B:
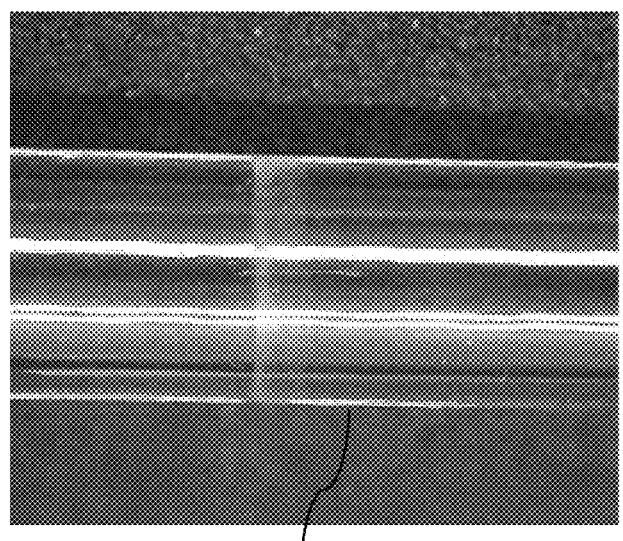
FIG. 16B shows a photograph of a syringe of the example 4 after transport simulation.
Figure 16A:
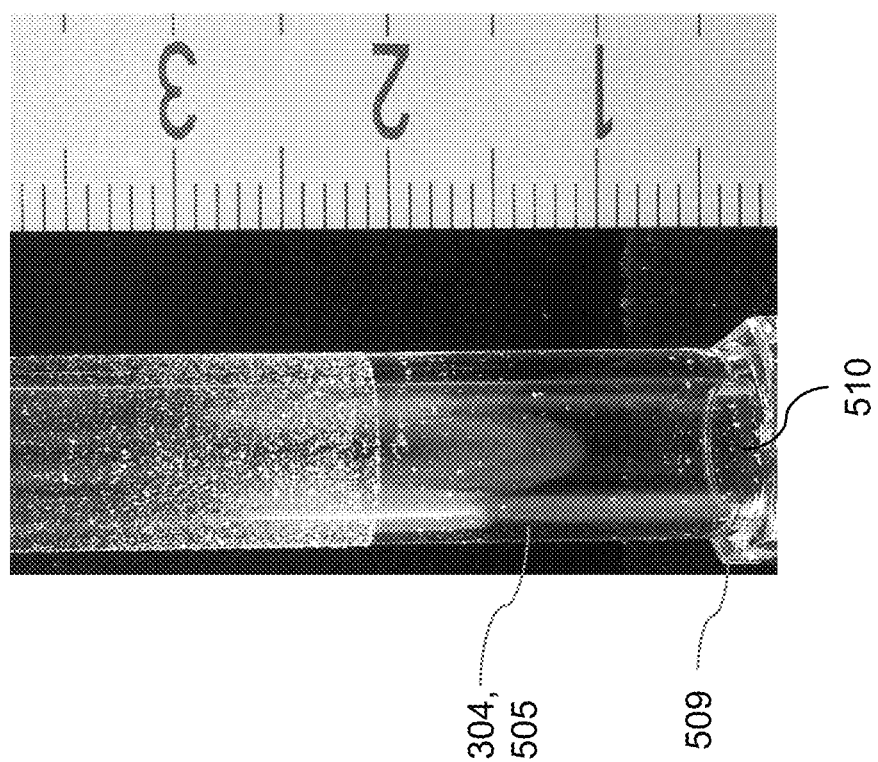
FIG. 16A shows a photograph of a syringe of the comparative example after transport simulation.

FIG. 16A shows a photograph of a primary packaging container 304. The latter is a syringe of the comparative example after transport simulation. Clearly, many macroscopic particles are present on the exterior surface of the container wall 505. At the bottom of FIG. 16A the rim 509 and the further orifice 510 of the syringe can be seen.

FIG. 16B shows a photograph of a further primary packaging container 304. This one is a syringe of the example 4 after transport simulation. In comparison to FIG. 16A, much less particles can be seen on the exterior surface of the container wall 505.

Figure 17A:
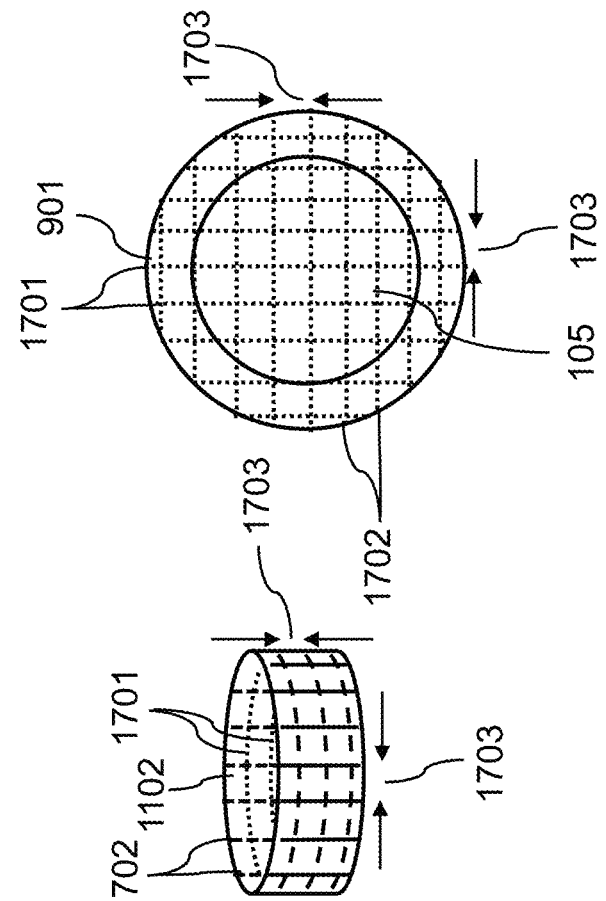
FIG. 17A illustrates determination of the total height $R_t$ of a roughness profile of an interior surface in each transversal section.

FIG. 17A illustrates determination of the maximum total height $R_t$ of roughness profiles of an interior surface 110 of a cylindrical receptacle. The interior surface 110 is fully covered with a grid of imaginary lines 1701 of a first multitude of equidistant lines and imaginary lines 1702 of a second multitude of equidistant lines. Two neighbouring equidistant lines have a distance 1703. $R_t$-values of each of the roughness profiles along the lines 1701 of the first multitude of equidistant lines and the lines 1702 of the second multitude of equidistant lines are determined. The maximum of these $R_t$-values is the maximum total height $R_t$ of roughness profiles of the interior surface 110.

Figure 17B:
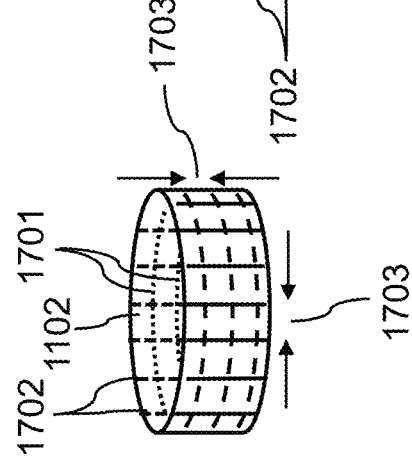
FIG. 17B illustrates determination of the total height $R_t$ of a roughness profile of a lateral surface of a retaining part in each transversal section.

FIG. 17B illustrates determination of the maximum total height $R_t$ of roughness profiles of a lateral surface 1102 of a retaining part 1101. The retaining part 1101 has the shape of a hollow cylinder. Such a retaining part 1101 can be seen in FIG. 12. The lateral surface 1102 of the retaining part 1101 is the interior surface of the hollow cylinder. Thus, the lateral surface 1102 is cylindrical. The lateral surface 1102 is fully covered with a grid of imaginary lines 1701 of a first multitude of equidistant lines and imaginary lines 1702 of a second multitude of equidistant lines. Two neighbouring equidistant lines have a distance 1703. $R_t$-values of each of the roughness profiles along the lines 1701 of the first multitude of equidistant lines and the lines 1702 of the second multitude of equidistant lines are determined. The maximum of these $R_t$-values is the maximum total height $R_t$ of roughness profiles of the lateral surface 1102 of the retaining part 1101.

Figure 17C:
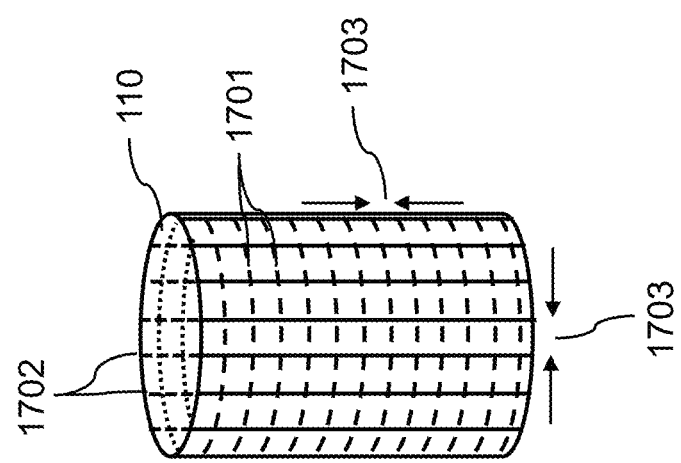
FIG. 17C illustrates determination of each roughness profile of an intermediate surface.

FIG. 17C illustrates determination of the maximum total height $R_t$ of roughness profiles of an intermediate surface 901. Such intermediate surfaces 901 can be seen at the first end 108 and the further end 202 of the receptacle 103 as shown in FIG. 9A. Those intermediate surfaces 901 are of the shape of an annulus. In FIG. 17C, the intermediate surface 901 surrounds the receptacle interior 105. The intermediate surface 901 is fully covered with a rectangular grid of imaginary lines 1701 of a first multitude of equidistant lines and imaginary lines 1702 of a second multitude of equidistant lines. Two neighbouring equidistant lines have a distance 1703. For each of the lines 1701 and 1702, the total height $R_t$ of the roughness profile along this line is determined. The maximum of these $R_t$-values is the maximum total height $R_t$ of roughness profiles of the intermediate surface 901.

LIST OF REFERENCE NUMERALS 100 holding device according to the invention
101 plate-shaped carrier element
102 through-hole
103 receptacle
104 receptacle wall
105 receptacle interior
106 longitudinal direction
107 first opening 108 first end
109 first edge
110 interior surface
111 exterior surface
112 length
113 width
201 further opening
202 further end
203 further edge
300 transport unit according to the invention
301 arrangement according to the invention
302 secondary packaging container
303 lid
304 primary packaging container
501 first end part
502 body part
503 further end part
504 discharge orifice
505 container wall
506 container interior
507 male part of Luer taper
508 stopper
509 rim
510 further orifice
511 plunger
601 flange
602 neck
603 shoulder
604 heel
605 standing base
700 process of producing the holding device according to the invention
701 process step a)
702 process step b)
703 process step c)
704 process step d)
705 process step e)
801 lateral directions
901 intermediate surface
902 plane of transversal section
903 central longitudinal axis
904 transversal section
1101 retaining part
1102 lateral surface
1500 optical microscope image
1501 burr
1701 lines of first multitude of equidistant lines
1702 lines of second multitude of equidistant lines
1703 distance between neighbouring equidistant lines While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A holding device for holding a plurality of primary packaging containers for pharmaceutical, medical, or cosmetic compositions, the holding device comprising:
a plate-shaped carrier element which includes a plurality of through-holes;
a plurality of receptacles, each of which is configured for accommodating a respective one of the plurality of primary packaging containers, each of the plurality of receptacles including a longitudinal direction and a receptacle wall which partially encloses a receptacle interior and forms a wall body, the wall body extending in the longitudinal direction through a respective one of the plurality of through-holes and, for each of the plurality of receptacles, having an interior surface which faces the receptacle interior and an exterior surface which faces opposite to the interior surface, at least 50% of respective ones of the plurality of receptacles having a maximum total height $R_t$ of a roughness profile of the interior surface which is not more than 0.50 mm, each of the plurality of receptacles including a first end and a second end, the wall body including a first opening at the first end, a second opening at the second end which, in the longitudinal direction, is opposite to the first end, at least one first edge, and at least one second edge, the first opening of the wall body being laterally directly surrounded by the at least one first edge, the second opening of the wall body being laterally directly surrounded by the at least one second edge.

2. The holding device according to claim 1, wherein the maximum total height $R_t$ of the roughness profile of the interior surface is not more than 0.40 mm.

3. The holding device according to claim 1, wherein the maximum total height $R_t$ of the roughness profile of the interior surface is not more than 0.30 mm.

4. The holding device according to claim 1, wherein the maximum total height $R_t$ of the roughness profile of the interior surface is not more than 0.20 mm.

5. The holding device according to claim 1, wherein the maximum total height $R_t$ of the roughness profile of the interior surface is not more than 0.10 mm.

6. The holding device according to claim 1, wherein at least 60% of respective ones of the plurality of receptacles have the maximum total height $R_t$ of the roughness profile of the interior surface.

7. The holding device according to claim 1, wherein at least 70% of respective ones of the plurality of receptacles have the maximum total height $R_t$ of the roughness profile of the interior surface.

8. The holding device according to claim 1, wherein at least 80% of respective ones of the plurality of receptacles have the maximum total height $R_t$ of the roughness profile of the interior surface.

9. The holding device according to claim 1, wherein at least 90% of respective ones of the plurality of receptacles have the maximum total height $R_t$ of the roughness profile of the interior surface.

10. The holding device according to claim 1, wherein at least 50% of respective ones of the plurality of receptacles have a total height $R_t$ of a roughness profile of at least one of the at least one first edge and the at least one second edge which is not more than 0.50 mm.

11. The holding device according to claim 1, wherein, for each of the plurality of receptacles, the wall body includes a retaining part which extends laterally, limits the receptacle interior in the longitudinal direction or in a counter-direction of the longitudinal direction, and includes the first opening or the second opening.

12. The holding device according to claim 11, wherein the retaining part includes a lateral surface, wherein, for each of the plurality of receptacles, the first opening or the second opening is laterally limited by the lateral surface of the retaining part, wherein at least 50% of respective ones of the plurality of receptacles have a maximum total height $R_t$ of a roughness profile of the lateral surface of the retaining part of not more than 0.50 mm.

13. The holding device according to claim 12, wherein at least 70% of respective ones of the plurality of receptacles have a maximum total height $R_t$ of a roughness profile of the lateral surface of the retaining part.

14. The holding device according to claim 12, at least 90% of respective ones of the plurality of receptacles have a maximum total height $R_t$ of a roughness profile of the lateral surface of the retaining part.

15. The holding device according to claim 1, wherein the plurality of primary packaging containers are selected from the group consisting of: vials; syringes; cartridges; ampoules; or a combination of at least two thereof.

16. A holding device for holding a plurality of primary packaging containers for pharmaceutical, medical, or cosmetic compositions, the holding device comprising:
a plate-shaped carrier element which includes a plurality of through-holes;
a plurality of receptacles, each of which is configured for accommodating a respective one of the plurality of primary packaging containers, each of the plurality of receptacles including a longitudinal direction and a receptacle wall which partially encloses a receptacle interior and forms a wall body, the wall body extending in the longitudinal direction through a respective one of the plurality of through-holes and, for each of the plurality of receptacles, having an interior surface which faces the receptacle interior and an exterior surface which faces opposite to the interior surface, at least 50% of respective ones of the plurality of receptacles having a maximum total height $R_t$ of a roughness profile of the interior surface which is not more than 0.50 mm, wherein, for each of the plurality of receptacles, the wall body includes at least one intermediate surface which (a) is neither part of the interior surface nor of the exterior surface, and (b) faces in the longitudinal direction or in a counter-direction of the longitudinal direction, wherein at least 50% of respective ones of the plurality of receptacles have a maximum total height $R_t$ of a roughness profile of the at least one intermediate surface of not more than 0.50 mm.

17. The holding device according to claim 16, wherein at least 70% of respective ones of the plurality of receptacles have a maximum total height $R_t$ of a roughness profile of the at least one intermediate surface.

18. The holding device according to claim 16, wherein at least 90% of respective ones of the plurality of receptacles have a maximum total height $R_t$ of a roughness profile of the at least one intermediate surface.

19. A transport unit, comprising:
an arrangement including:
a holding device for holding a plurality of primary packaging containers for pharmaceutical, medical, or cosmetic compositions, the holding device comprising:
a plate-shaped carrier element which includes a plurality of through-holes;
a plurality of receptacles, each of which is configured for accommodating a respective one of the plurality of primary packaging containers, each of the plurality of receptacles including a longitudinal direction and a receptacle wall which partially encloses a receptacle interior and forms a wall body, the wall body extending in the longitudinal direction through a respective one of the plurality of through-holes and, for each of the plurality of receptacles, having an interior surface which faces the receptacle interior and an exterior surface which faces opposite to the interior surface, at least 50% of respective ones of the plurality of receptacles having a maximum total height $R_t$ of a roughness profile of the interior surface which is not more than 0.50 mm, each of the plurality of receptacles including a first end and a second end, the wall body including a first opening at the first end, a second opening at the second end which, in the longitudinal direction, is opposite to the first end, at least one first edge, and at least one second edge, the first opening of the wall body being laterally directly surrounded by the at least one first edge, the second opening of the wall body being laterally directly surrounded by the at least one second edge;
the plurality of primary packaging containers, each of which is accommodated respectively in one of the plurality of receptacles; and
a secondary packaging container, the holding device and the plurality of primary packaging containers being arranged completely in the secondary packaging container.

\* \* \* \* \*